(12) United States Patent
Nichols et al.

(10) Patent No.: US 7,744,890 B2
(45) Date of Patent: Jun. 29, 2010

(54) METHODS AND COMPOSITIONS WITH REDUCED OPALESCENCE

(75) Inventors: Pilarin Elizabeth Nichols, Andover, MA (US); Donna L. Luisi, North Andover, MA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/974,312

(22) Filed: Oct. 12, 2007

(65) Prior Publication Data

US 2008/0154023 A1 Jun. 26, 2008

Related U.S. Application Data

(60) Provisional application No. 60/851,651, filed on Oct. 12, 2006.

(51) Int. Cl.
*A61K 39/395* (2006.01)
*C07K 16/00* (2006.01)
*C07K 1/34* (2006.01)

(52) U.S. Cl. .................. 424/177.1; 530/390.5; 530/414; 530/417

(58) Field of Classification Search ........................ None
See application file for complete search history.

(56) References Cited

U.S. PATENT DOCUMENTS

| | | | |
|---|---|---|---|
| 4,396,608 A * | 8/1983 | Tenold ..................... 424/177.1 |
| 4,399,216 A | 8/1983 | Axel et al. | |
| 4,510,245 A | 4/1985 | Cousens et al. | |
| 4,522,811 A | 6/1985 | Eppstein et al. | |
| 4,634,665 A | 1/1987 | Axel et al. | |
| 4,704,362 A | 11/1987 | Itakura et al. | |
| 4,816,397 A | 3/1989 | Boss et al. | |
| 4,816,567 A | 3/1989 | Cabilly et al. | |
| 4,849,508 A * | 7/1989 | Magnin et al. ........... 424/161.1 |
| 4,968,615 A | 11/1990 | Koszinowski et al. | |
| 5,168,062 A | 12/1992 | Stinski | |
| 5,179,017 A | 1/1993 | Axel et al. | |
| 5,223,409 A | 6/1993 | Ladner et al. | |
| 5,225,538 A | 7/1993 | Capon et al. | |
| 5,225,539 A | 7/1993 | Winter et al. | |
| 5,304,489 A | 4/1994 | Rosen | |
| 5,428,130 A | 6/1995 | Capon et al. | |
| 5,455,165 A | 10/1995 | Capon et al. | |
| 5,514,582 A | 5/1996 | Capon et al. | |
| 5,516,964 A | 5/1996 | Umansky et al. | |
| 5,549,892 A | 8/1996 | Friedman et al. | |
| 5,585,089 A | 12/1996 | Queen et al. | |
| 5,693,761 A | 12/1997 | Queen et al. | |
| 5,693,762 A | 12/1997 | Queen et al. | |
| 5,714,147 A | 2/1998 | Capon et al. | |
| 5,741,957 A | 4/1998 | Deboer et al. | |
| 5,786,160 A | 7/1998 | Anderson et al. | |
| 5,849,992 A | 12/1998 | Meade et al. | |
| 5,859,205 A | 1/1999 | Adair et al. | |
| 5,994,511 A * | 11/1999 | Lowman et al. ........... 530/387.3 |
| 6,193,980 B1 | 2/2001 | Efstathiou et al. | |
| 6,238,664 B1 * | 5/2001 | Hellerbrand et al. ..... 424/130.1 |
| 6,281,336 B1 * | 8/2001 | Laursen et al. ........... 530/390.1 |
| 6,300,064 B1 | 10/2001 | Knappik et al. | |
| 6,407,213 B1 | 6/2002 | Carter et al. | |
| 6,939,545 B2 | 9/2005 | Jacobs et al. | |
| 2002/0157125 A1 | 10/2002 | Lee et al. | |
| 2003/0018004 A1 | 1/2003 | Kingsman et al. | |
| 2003/0070185 A1 | 4/2003 | Jakobovits et al. | |
| 2003/0108549 A1 | 6/2003 | Carter et al. | |
| 2003/0165496 A1 | 9/2003 | Basi et al. | |
| 2004/0082762 A1 | 4/2004 | Basi et al. | |
| 2004/0082764 A1 | 4/2004 | Kunz et al. | |
| 2004/0087777 A1 | 5/2004 | Basi et al. | |
| 2004/0142382 A1 * | 7/2004 | Veldman et al. ............... 435/7.1 |
| 2004/0197324 A1 * | 10/2004 | Liu et al. .................. 424/130.1 |
| 2005/0032216 A1 | 2/2005 | Kingsman et al. | |
| 2005/0042220 A1 | 2/2005 | Li et al. | |
| 2005/0100958 A1 | 5/2005 | Stern et al. | |
| 2005/0118651 A1 | 6/2005 | Basi et al. | |
| 2005/0136049 A1 | 6/2005 | Ledbetter et al. | |
| 2005/0158760 A1 | 7/2005 | Jacobs et al. | |
| 2005/0249725 A1 | 11/2005 | Schenk et al. | |
| 2006/0063228 A1 | 3/2006 | Kasaian et al. | |
| 2006/0073148 A1 | 4/2006 | Tchistiakova et al. | |
| 2006/0088522 A1 | 4/2006 | Boghaert et al. | |

FOREIGN PATENT DOCUMENTS

| EP | 171496 | 2/1986 |
|---|---|---|
| EP | 0173494 | 3/1986 |
| EP | 0239400 | 9/1987 |

(Continued)

OTHER PUBLICATIONS

International Search Report to PCT/US2007/021904 dated Apr. 4, 2008.

(Continued)

*Primary Examiner*—David A Saunders
(74) *Attorney, Agent, or Firm*—Mabel Ng

(57) ABSTRACT

Methods for reducing the opalescent appearance of a protein preparation by modifying the ionic strength of the preparation, as well as compositions, e.g., pharmaceutical compositions, of concentrated protein with decreased opalescence are disclosed. Purification methods which monitor and/or reduce the salt concentrations at selected steps are also disclosed.

40 Claims, 9 Drawing Sheets

FOREIGN PATENT DOCUMENTS

| EP | 417014 | 3/1991 |
|---|---|---|
| EP | 417563 | 3/1991 |
| GB | 2177096 | 1/1987 |
| WO | WO-8907947 | 9/1989 |
| WO | WO-90/02809 | 3/1990 |
| WO | WO-9111172 | 8/1991 |
| WO | WO-91/17271 | 11/1991 |
| WO | WO-9201047 | 1/1992 |
| WO | WO-9206193 | 4/1992 |
| WO | WO-92/09690 | 6/1992 |
| WO | WO-92/15679 | 9/1992 |
| WO | WO-92/18619 | 10/1992 |
| WO | WO-92/20791 | 11/1992 |
| WO | WO-93/01288 | 1/1993 |
| WO | WO-9402518 | 2/1994 |
| WO | WO-96/33735 | 10/1996 |
| WO | WO-96/34096 | 10/1996 |
| WO | WO-98/52976 | 11/1998 |
| WO | WO-9855148 | 12/1998 |
| WO | WO-0029428 | 5/2000 |
| WO | WO-0034317 | 6/2000 |
| WO | WO-0136486 | 5/2001 |
| WO | WO-0162801 | 8/2001 |
| WO | WO-0246237 | 6/2002 |
| WO | WO-02088306 | 11/2002 |
| WO | WO-02088307 | 11/2002 |
| WO | WO-03077858 | 9/2003 |
| WO | WO-2004/091658 | 10/2004 |
| WO | WO-2004108895 | 12/2004 |
| WO | WO-2008/045563 | 4/2008 |

OTHER PUBLICATIONS

Written Opinion of the International Searching Authority to PCT/US2007/021904 dated .

Bajaj Harminder et al, "Protein structural conformation and not second viral coefficient relates to long-term irreversible aggregation of monoclonal antibody and ovalbumin in solution.", *Pharmaceutical Research*, Jun. 2006, pp. 1382-1394, vol. 23, No. 6.

Sisti A M et al, "Preparation of lyophilized and liquid intravenous immunoglobulin G: Development and scale-up", *Vox Sanguinis*, May 2001, pp. 216-224, vol. 80, No. 4.

A. Wilcox, J. Guo, T. Spitznagel, R. Krishnamurthy, "Opalescence of a Monoclonal Antibody and its Dependence on Ionic Strength and Temperature", 2005 AAPS Annual Meeting and Exposition, Nov. 2005.

Chi Eva Y et al, "Physical stability of proteins in aqueous solution: Mechanism and driving forces in nonnative protein aggregation", *Pharmaceutical Research (Dordrecht)*, Sep. 2003, pp. 1325-1336, vol. 20, No. 9.

Harris Reed J et al, "Commercial manufacturing scale formulation and analytical characterization of therapeutic recombinant antibodies", *Drug Development Research*, Mar. 2004, pp. 137-154, vol. 61, No. 3.

Ahrer et al, "Thermodynamic stability and formation of aggregates of human immunoglobulin G characterised by differential scanning calorimetry and dynamic light scattering", *Journal of Biochemical and Biophysical Methods*, Mar. 2006, pp. 73-86, vol. 66, Nos. 1-3.

Liu J et al, Reversible self-association increases the viscosity of a concentrated monoclonal antibody in aqueous solution, *Journal of Pharmaceutical Sciences*, Sep. 2005, pp. 1928-1940, vol. 94, p. 9.

Fatouros Angelica et al, "Recombinant factor VIII SQ: Influence of oxygen, metal ions, pH and ionic strength on its stability in aqueous solution", *International Journal of Pharmaceutics*, 1997, pp. 121-131, vol. 155, No. 1.

Wang Wei, "Instability, stabilization, and formulation of liquid protein pharmaceuticals", *International Journal of Pharmaceutics*, Aug. 1999, pp. 129-188, vol. 185, No. 2.

Wang W, "Protein aggregation and its inhibition in biopharmaceutics", *International Journal of Pharmaceutics*, Jan. 2005, pp. 1-30, vol. 289, Nos. 1-2.

Izutsu Ken-Ichi, "Stabilization of therapeutic proteins by chemical and physical methods", *Methods in Molecular Biology*, 2005, pp. 287-292, vol. 308.

Schreiber Gideon, "Kinetic studies of protein-protein interactions", *Current Opinion in Structural Biology*, Feb. 2002, pp. 41-47, vol. 12, No. 1.

Anonymous, "Workshop on Protein Aggregation—Summary of Responses to Questions for Breakout Sessions", Internet Article retrieved from the Internet: URL:http://www.aapspharmaceutica.com/inside/Focus_Groups/ProteinAgg/imagespdfs/ProteinWrkshpBOInfo2006.pdf, Sep. 2006.

Brekke, O.H. and Sandlie, I., "Therapeutic antibodies for human diseases at the dawn of the twenty-first century", Nat. Rev. Drug Discov., 2003, vol. 2, pp. 52-62.

Schellekens, H., "Bioequivalence and the immunogenicity of biopharmaceuticals", Nat. Rev. Drug Discov., 2002, vol. 1, pp. 457-462.

Pinckard et al., "Factors influencing the immune response: Effects of the physical state of the antigen and of lymphoreticular cell proliferation on the response to intraperitoneal injection of bovine serum albumin in rabbits", Clin Exp. Immunol., 1967, vol. 2, pp. 331-340.

Robbins et al., "Antibodies to covalent aggregates of insulin in blood of insulin-using diabetic patients", Diabetes, 1987, vol. 36, pp. 838-845.

Cleland et al., "The development of stable protein formulations: a close look at protein aggregation, deamidation, and oxidation", Crit. Rev. Therapeutic Drug Carrier Systems, 1993, vol. 10, p. 307-377.

Miro, M. et al., Analytica Chimica Acta, 2004, vol. 512, No. 2, pp. 311-317.

Tessier, P.M. et al., "Measurements of protein self-association as a guide to crystallization", Current Opinion in Biotechnology, 2003, vol. 14, No. 5, pp. 512-516.

Eckhardt, B.M., "A turbidimetric method to determine visual appearance of protein solutions", J. Pharm Sci Technol., 1994, vol. 48, No. 2, pp. 64-70.

Giddings, J.C., Yang, F.J., Myers, M.N., "Flow-field-flow fractionation: a versatile new separation method," Science, 1976, vol. 193, pp. 1244-1245.

Giddings, J.C., Yang, F.J., Myers, M.N., "Theoretical and experimental characterization of flow field-flow fractionation," Anal. Chem., 1976, vol. 48, pp. 1126-1132.

Zimm, B., "The scattering of light and the radial distribution function of high polymer solutions," J. Chem. Phys., 1948, vol. 16, pp. 1093-1099.

Chothia, D. et al., "Structural repertoire of the human VH segments", J. Mol. Biol., 1992, vol. 227, pp. 799-817.

Tomlinson et al., "The structural repertoire of the human V kappa domain", EMBO J., 1995, vol. 14, pp. 4628-4638.

Bird et al., Science, 1988, vol. 242, pp. 423-426.

Huston et al., Proc. Natl. Acad. Sci. U.S.A., 1988, vol. 85, pp. 5879-5883.

Songsivilai & Lachmann, Clin. Exp. Immunol., 1990, vol. 79, pp. 315-321.

Kostelny et al., J. Immunol., 1992, vol. 148, pp. 1547-1553.

Smith, Science, 1985, vol. 228, pp. 1315-1317.

Green et al., Nature Genetics, 1994, vol. 7, pp. 13-21.

Morrison et al., Proc. Natl. Acad. Sci. U.S.A., 1985, vol. 81, p. 6851.

Takeda et al., Nature, 1985, vol. 314, p. 452.

Morrison, Science, 1985, vol. 229, pp. 1202-1207.

Oi et al., BioTechniques, 1986, vol. 4, p. 214.

Teng et al., Proc. Natl. Acad. Sci. U.S.A., 1983, vol. 80, pp. 7308-7312.

Kozbor et al., Immunology Today, 1983, vol. 4, p. 7279.

Olsson et al., Meth. Enzymol., 1982, vol. 92, pp. 3-16.

Tomlinson et al., J. Mol. Biol., 1992, vol. 227, pp. 776-798.

Cook, G.P. et al., Immunol. Today, 1995, vol. 16, No. 5, pp. 237-242.

Ravetch and Kinet, Annu. Rev. Immunol, 1991, vol. 9, pp. 457-492.

Capel et al., Immunomethods, 1994, vol. 4, pp. 25-34.

De Haas et al., J. Lab. Clin. Med., 1995, vol. 126, pp. 330-341.

McPherron et al., Proc. Nat. Acad. Sci. U.S.A., 1997, vol. 94, pp. 12457-12461.

Myers et al., J Biol Chem, 1994, vol. 169, pp. 9319-9324.
Starzynska et al., Eur. J. Gastroenterol. Hepatol., 1998, vol. 10, pp. 479-484.
Starzynska et al., Br. J. Cancer, 1994, vol. 69, pp. 899-902.
Starzynska et al., Br. J. Cancer, 1992, vol. 66, pp. 867-869.
Carsberg et al., Int J Cancer. 1996, vol. 68, pp. 84-92.
McKenzie et al., Proc. Natl. Acad. Sci. USA, 1993, vol. 90, pp. 3735-3739.
Bost et al., Immunology, 1996, vol. 87, pp. 663-641.
Tomkinson et al., J. Immunol., 2001, vol. 166, pp. 5792-5800.
Sanchez-Guererro et al., Allergy, 1994, vol. 49, pp. 587-592.
Dilorenzo et al., Allergy Asthma Proc., 1999, vol. 20, pp. 119-125.
Wills-Karp et al., Science, 1998, vol. 282, pp. 2258-2261.
Dumoutier L. et al., Proc Natl Acad Sci USA, 2000, vol. 97, No. 18, pp. 10144-10149.

Pittman D. et al., Genes and Immunity, 2001, vol. 2, p. 172.
Naismith and Sprang, J. Inflamm., 1995-96, vol. 47, Nos. 1-2, pp. 1-7.
Elliott et al., Nature Biotechnology, 2003, vol. 21, No. 4, pp. 414-421.
Chang et al., J. Clin. Invest., 1997, vol. 100, Issue 4, p. 886.
Graham et al., J. Gen Virol., 1977, vol. 36, p. 59.
Urlaub and Chasin, Proc. Natl. Acad. Sci. USA, 1980, vol. 77, p. 4216.
Mather, Biol. Reprod., 23:243-251, 1980.
Mather et al., Annals N.Y. Acad. Sci., 383:44-68, 1982.
Queen et al., Immunol. Rev., 1986, vol. 89, p. 49.
Co et al., J. Immunol., 1992, vol. 148, p. 1149.
McCutchen-Maloney et al. Journal of Biol. Chem. 2000, vol. 275, pp. 18557-18565.

* cited by examiner

A plot of OD400 nm versus Antibody M1 concentrtion in 20 mM CaCl$_2$

US 7,744,890 B2

METHODS AND COMPOSITIONS WITH REDUCED OPALESCENCE

CROSS REFERENCE TO RELATED APPLICATIONS

This application claims priority to U.S. Application Ser. No. 60/851,651, filed on Oct. 12, 2006, the content of which is hereby incorporated by reference in its entirety.

TECHNICAL FIELD

The invention relates to methods for reducing the opalescence of protein preparations, as well as compositions, e.g., pharmaceutical compositions, of concentrated protein preparations having decreased opalescence.

BACKGROUND

Proteins, including antibodies, have been used in drug therapy for the past twenty years. In order to achieve high therapeutic doses, antibodies are typically formulated at high concentrations (about 10 mg/ml to 100 mg/ml or greater) (Brekke, O. H. and Sandlie, I. (2003) *Nat. Rev. Drug Discov.* 2:52-62). Certain modes of protein administration typically require highly concentrated protein formulations. For example, subcutaneous administration of therapeutic antibodies are often formulated at concentrations greater than about 100 mg/ml. Some of these concentrated protein formulations develop an opalescent appearance at high concentrations, a property often referred to as opalescence (Schellekens, H. (2002) *Nat. Rev. Drug Discov.* 1:457-462).

An opalescent appearance in a concentrated protein solution may result from a variety of factors, including protein concentration, its effect in Rayleigh scatter, temperature, the nature of solute-solute interactions, among others. When a protein is susceptible to opalescence, the opalescent appearance usually increases as the protein concentration increases. The similarity of opalescent solutions to aggregated protein solutions has raised concerns with respect to its loss of protein activity and potential to cause immunogenicity in pharmaceutical formulations (Pinckard et al. (1967) *Clin Exp. Immunol.* 2:331-340; Robbins et al. (1987) *Diabetes* 36:838-845; Cleland et al. (1993) *Crit. Rev. Therapeutic Drug Carrier Systems* 10:307-377).

Thus, there is a need for developing formulations of highly concentrated therapeutic proteins, e.g., therapeutic antibodies, having reduced opalescence.

SUMMARY

The invention is based, at least in part, on the discovery that reducing the concentration of salt, e.g., sodium chloride, in an antibody preparation reduces the opalescent appearance of the preparation and/or the formation of high molecular weight species in the preparation. Thus, methods of reducing the opalescent appearance of protein, e.g., antibody, preparations, e.g., by modifying the ionic strength of the preparations, as well as compositions, e.g., pharmaceutical compositions, of concentrated proteins having decreased opalescence are disclosed. Purification methods which monitor and/or reduce the salt concentration(s) at selected steps in the purification process are also disclosed.

Accordingly, in one aspect, the invention features a method for decreasing the opalescence of, or reducing the amount of high molecular weight species in, a protein preparation, e.g., an antibody preparation (e.g., a solution that includes a protein, e.g., an antibody). The method includes modifying, e.g., decreasing or increasing, the ionic strength of the preparation such that the opalescent appearance of, and/or the amount of high molecular weight species in, the protein preparation is reduced and/or eliminated. In embodiments, the ratio of the ionic strength to the protein concentration, e.g., the antibody concentration, in the protein preparation is modified or altered, e.g., decreased or increased, such that the opalescent appearance of, and/or the amount of high molecular weight species in, the protein preparation is reduced and/or eliminated. In embodiments, the protein preparation shows unwanted opalescence and/or high molecular weight species prior to reducing the ionic strength (e.g., a turbidity greater than about 1, 2, 3, 4 or 5, or more European Pharmacopeia standard and/or a percentage of high molecular weight species corresponding to about 2%, 3%, 5%, 10%, 15%, 20%, 30% or higher of the percent mass of the protein preparation) at a pharmaceutically effective concentration, e.g., about 5, 10, 25, 50, 75, 100, 125, 150 mg/ml for antibody preparations.

In embodiments, the protein in the preparation is a secreted protein, e.g., an antibody, an antigen-binding fragment of an antibody, a binding domain-immunoglobulin fusion (e.g., SMIP™), a soluble receptor, a receptor fusion, a cytokine, a growth factor, an enzyme, or a clotting factor, as described in more detail herein below. In embodiments where the protein is an antibody, it can include at least one, and preferably two full-length heavy chains, and at least one, and preferably two light chains. The term "antibody" as used herein includes an antibody fragment or a variant molecule such as an antigen-binding fragment (e.g., an Fab, F(ab')$_2$, Fv, a single chain Fv fragment, and a heavy chain fragment (e.g., a camelid VHH). The antibody can be a monoclonal or single-specificity antibody. The antibody can also be a human, humanized, chimeric, CDR-grafted, or in vitro generated antibody. In yet other embodiments, the antibody has a heavy chain constant region chosen from, e.g., IgG1, IgG2, IgG3, or IgG4. In another embodiment, the antibody has a light chain chosen from, e.g., kappa or lambda. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). Typically, the antibody specifically binds to a predetermined antigen, e.g., an antigen associated with a disorder, e.g., a neurodegenerative, metabolic, inflammatory, autoimmune and/or a malignant disorder. Exemplary antibodies that can be used in the methods of the invention include, but are not limited to, antibodies against an Aβ peptide, interleukin-12 (IL-12), interleukin-13 (IL-13), interleukin-22 (IL-22), 5T4, and growth and differentiation factor-8 (GDF-8). In embodiments, the antibody is an anti-GDF-8 antibody, e.g., Myo-029.

In embodiments, the protein self-aggregates at a higher protein and/or salt concentration, e.g., has a negative second virial coefficient, e.g., in a high salt preparation (e.g., a preparation having a salt concentration of about 50 to 200 mM (e.g., about 100 to 150 mM of a salt)). For example, the protein has a second virial coefficient of about $-1 \times 10^{-1}$ to $-1$, about $-1 \times 10^{-2}$ to $-10 \times 10^{-2}$, about $-1 \times 10^{-3}$ to $-10 \times 10^{-3}$, about $-1 \times 10^{-4}$ to $-10 \times 10^{-4}$, about $-1 \times 10^{-5}$ to $-10 \times 10^{-5}$ mol-mg/g$^2$ in a preparation containing, e.g., 150 mM sodium chloride. In other embodiments, the protein has a positive virial coefficient, e.g., about $1 \times 10^{-5}$ to $10 \times 10^{-5}$, about $1 \times 10^{-4}$ to $10 \times 10^{-4}$, about $1 \times 10^{-3}$ to $10 \times 10^{-3}$, about $1 \times 10^{-2}$ to $10 \times 10^{-2}$ mol-mg/g$^2$ in a preparation containing, e.g., 150 mM sodium chloride. In embodiments where the protein is an antibody or a fragment thereof, the antibody is present at a concentration of about 0.1 to about 1,000 mg/ml, typically about 0.5 to about 500, about 1 to 400, about 5 to 300, about 10 to 250, about 15 to 200, about 20 to 150, about 50 to 100 mg/ml prior to, and/or after practicing the methods of the invention.

In embodiments, the ionic strength of the protein preparation is modified, e.g., reduced, by decreasing the concentration of a salt present in the preparation, and/or by replacing the salt used in the preparation with a salt that induces less opalescence. The salt in the preparation can be chosen from one or more of, e.g., sodium chloride, calcium chloride, magnesium chloride or sodium phosphate. The salt concentration in the preparation can be reduced to a lower concentration, e.g., a concentration at least about two-, three-, five-, ten- or one hundred-fold lower than the concentration in the opalescent preparation. For example, the salt (e.g., sodium chloride) concentration in the protein preparation can be reduced to less than about, 300 mM, typically, less than about 200, 150, 100, 75, 50, 40, 30, 25, 20, 15, 10, 5, 4, 3, 2, 1 or 0 mM. The salt concentration in the protein preparation can be modified, e.g., reduced by, e.g., applying one or more filtration methods chosen from one or more of: ultra-filtration or dialysis. Alternatively or in addition, the ionic strength of the protein preparation is modified, e.g., decreased or increased, by replacing one or more first salt(s), e.g., a high opalescent inducer, with one or more second salt(s), e.g., a lower opalescent inducer. The following exemplary salts were ranked according to the level of opalescence induction in antibody preparations, in the following order from high to low opalescence inducer: sodium chloride (NaCl), sodium phosphate ($NaHPO_4$), magnesium chloride ($MgCl_2$) and calcium chloride ($CaCl_2$). Accordingly, in embodiments, the first salt is NaCl, and is replaced with a second salt chosen from one or more of, e.g., $NaHPO_4$, $MgCl_2$, or $CaCl_2$; the first salt is $NaHPO_4$, and is replaced with a second salt chosen from one or more of, e.g., $MgCl_2$ or $CaCl_2$; the first salt is $MgCl_2$, and is replaced with a second salt, $CaCl_2$ In embodiments, the first salt is replaced by the second salt in the protein preparation by removing the first salt, e.g., by dialysis or ultrafiltration, and adding the second salt to the protein preparation. In embodiments, the concentration of the second salt is greater than the concentration of the first salt. In embodiments, the concentration of the second salt is equal to the concentration of the first salt. In other embodiments, the concentration of the second salt is less than the concentration of the first salt.

In other embodiments, the ionic strength of the protein preparation is modified, e.g., decreased or increased, in the process of making and/or purifying the protein, e.g., by decreasing the concentration of a high opalescent inducer salt used. The embodiments include: (i) (optionally) evaluating whether the protein preparation forms an opalescent solution at one or more protein and/or salt concentrations; (ii) (optionally) providing the salt concentration in the protein preparation; and/or (iii) modifying, e.g., reducing, the ionic strength of the protein preparation (e.g., modifying the ratio of the ionic strength to the protein concentration in the protein preparation). Steps (ii) and/or (iii) can be repeated and/or carried out in any order, as needed. Step (i) can be performed by detecting the opalescence and/or presence of high molecular weight species in one or more samples containing different concentrations of the protein and/or salt, for example, as described in the Examples herein. The ionic strength of the protein preparation can be modified, e.g., reduced, e.g., by applying one or more filtration methods described herein. Alternatively or in addition, the ionic strength of the protein preparation can be decreased by reducing the ionic strength, e.g., the salt concentration, of one or more steps in the process of making and/or purifying the protein. Such reduction in ionic strength in the process of making and/or purifying the protein can be effected by decreasing the concentration of a salt used in the one or more steps. In other embodiments, the ionic strength is modified by replacing the salt used in the one or more steps with a lower opalescent inducer. In certain embodiments, the protein in the preparation is made recombinantly, e.g., expressed using recombinant techniques as, e.g., a cell-bound, a soluble or a secreted protein. In such embodiments, the protein is expressed and separated from the recombinant host (e.g., secreted into the medium and separated, by, e.g., centrifugation or filtration). The separated protein is further purified by methods known in the art, including, but not limited to, Protein A chromatography, affinity chromatography, hydrophobic interaction chromatography, immobilized metal affinity chromatography, size exclusion chromatography, diafiltration, ultrafiltration, viral removal filtration, anion exchange chromatography, hydroxyapatite chromatography and/or cation exchange chromatography. The protein may be further lyophilized and/or reconstituted in a buffer solution. The methods of the invention include modifying, e.g., reducing, the ionic strength, e.g., the salt concentration, of the solutions (e.g., washing, load, elution, reconstitution solutions), used in one or more of the aforesaid steps.

Without being bound by theory, it is believed that residual amounts of salt can be present in protein preparations, even after applying filtration methods such as ultra-filtration and dialysis. Such residual salt amounts are characterized in the art as the "Donnan effect." (Miro, M et al. (2004) *Analytica Chimica Acta* 512(2):311-317). It is believed that such residual salt amounts might lead to protein preparations having an opalescent appearance, particularly when the protein in the preparation has a tendency to self-aggregate, e.g., it has a negative virial coefficient. Thus, modifying the ionic concentration using the methods disclosed herein can have broad applicability to protein purification techniques.

In embodiments, the reduction in opalescence of the protein preparation is detected by evaluating the turbidity of the solution. For example, the turbidity of the protein preparation is reduced to about 5, 4, 3, 2, 1 or less European Pharmacopeia standard.

In other embodiments, the reduction in opalescence of the protein preparation is determined by evaluating a change in the second virial coefficient of the protein. For example, a two-, three-, five-, ten- or one hundred-fold change, e.g., an increase or a decrease in the second virial coefficient of the protein is detected after modifying, e.g., reducing, the ionic strength of the protein preparation. For example, the virial coefficient changes, e.g., decreases, from anywhere between about $1 \times 10^{-2}$ and $1 \times 10^{-3}$ to anywhere between about $1 \times 10^{-3}$ and $1 \times 10^{-4}$ In yet other embodiments, the reduction in opalescence in the protein preparation is detected by determining the amount of high molecular weight species. The high molecular weight species typically have a molecular weight of about $10^4$, more typically, about $10^5$, $10^6$, $10^7$, $10^8$, $10^9$, $10^{10}$, $10^{11}$, $10^{12}$, $10^{13}$, or higher. The weight average molecular weight of the protein species in the preparation can be detected using one or more of: light scattering techniques, e.g., static and dynamic light scattering, asymmetric flow field flow fractionation, or SEC-HPLC, as, for example, described in the Examples below. In embodiments, a two-, three-, four-, five-, six-, seven-, eight-, nine-, ten-, fifty- or one hundred-fold decrease in high molecular weight species is indicative of a reduction of opalescence in the protein preparation. For example, the percentage mass of the high molecular weight species decreased from about 30 to 40% of the total protein mass to less than about 5%, with a concomitant increase in the percentage mass of the non-aggregated protein from about 60 to 70% of the total protein mass to about 95% or higher (as detected by dynamic light scattering).

In another aspect, the invention features a method of decreasing the formation, and/or reducing the amount, of high molecular weight species in a protein, e.g., antibody, preparation (e.g., a protein, e.g., antibody, preparation as described herein). The method includes modifying, e.g., decreasing or increasing, the ionic strength of the preparation (e.g., modifying the ratio of the ionic strength to the protein concentration in the protein preparation), such that the amount of high molecular weight species in the protein preparation is reduced and/or eliminated.

In embodiments, the high molecular weight species are protein aggregates, which can be substantially reversibly dissociated upon reducing the protein and/or salt concentration. The high molecular weight species typically have a molecular weight of about $10^4$ kDa, more typically, about $10^5$, $10^6$, $10^7$, $10^8$, $10^9$, $10^{10}$, $10^{11}$, $10^{12}$, $10^{13}$ kDa, or higher. The weight average molecular weight of the protein species in the preparation can be detected using one or more of: light scattering techniques, e.g., static and dynamic light scattering, asymmetric flow field flow fractionation, or SEC-HPLC, as, for example, described in the Examples below. In embodiments, a two-, three-, four-, five-, six-, seven-, eight-, nine-, ten-, fifty- or one hundred-fold decrease in high molecular weight species is indicative of a reduction of opalescence in the protein preparation. For example, the percentage mass of the higher molecular weight species is decreased from about 30 to 40% of the total protein mass to less than about 5%, with a concomitant increase in the percentage mass of the non-aggregated protein from about 60 to 70% of the total protein mass to about 95% or higher (as detected by dynamic light scattering).

In embodiments, the decrease in ionic strength of the preparation is effected by the methods disclosed herein.

In another aspect, the invention features a method of improving the efficiency of a production and/or purification process of a protein, e.g., antibody, preparation (e.g., a protein, e.g., antibody, preparation as described herein). The method includes: (i) (optionally) evaluating whether the protein preparation forms an opalescent solution at one or more protein and/or salt concentrations; (ii) modifying, e.g., decreasing, the ionic strength of the preparation, such that the amount of high molecular weight species in the protein preparation is reduced and/or eliminated. Step (i) can be performed by detecting the opalescence and/or presence of high molecular weight species in one or more samples containing different concentrations of the protein and/or salt, for example, as described in the Examples herein. The ionic strength of the protein preparation can be modified, e.g., reduced, e.g., by applying one or more filtration methods described herein; replacing the salt used in the protein preparation with a lower opalescent inducer, e.g., as described herein; and/or reducing the ionic strength of one or more steps in the process of making and/or purifying the protein, e.g., as described herein.

In yet another aspect, the invention features a method of improving the production of an antibody, e.g., selecting a salt or a salt concentration for use in a process of making an antibody. The method includes (i) recovering an antibody solution (e.g., eluting an antibody from a matrix; recovering a dialyzed solution or other filtrate; and/or solubilizing a dry preparation, e.g., a lyophilized or dried preparation with a first solution having a first ionic strength, e.g., first salt concentration); (ii) evaluating the level of opalescence and/or presence of high molecular weight species in the antibody solution;

wherein (a) if the level of opalescence and/or high molecular weight species is equal to or less than a predetermined level, then selecting said antibody solution for use in the antibody product, e.g., a pharmaceutical composition that includes the antibody solution; or (b) if the level of opalescence and/or high molecular weight species is greater than a predetermined level, then selecting a second solution having a second, e.g., lower, ionic strength (e.g., a second, e.g., lower, salt concentration). The level of opalescence and/or presence of high molecular weight species in the second solution containing the antibody can be evaluated, as needed, and additional solutions can be added until the level of opalescence reaches (or is less than) the predetermined level.

In embodiments, the antibody solution is recovered from one or more protein purification methods known in the art, including, but not limited to, Protein A chromatography, affinity chromatography, hydrophobic interaction chromatography, immobilized metal affinity chromatography, size exclusion chromatography, diafiltration, ultrafiltration, viral removal filtration, anion exchange chromatography, hydroxyapatite chromatography and/or cation exchange chromatography. The protein may be further lyophilized and/or reconstituted in a buffer solution.

In embodiments, the predetermined level of the antibody (first, second and additional) solution is a turbidity value of about greater than about 1, 2, 3, 4, 5 or more European Pharmacopeia standard, typically about 3, and/or an increase in high molecular weight species to 1%, 2%, 3%, 5%, 10%, 15%, 20%, 30% or higher of the percent mass of the protein preparation, typically about 2% at a pharmaceutically effective concentration, e.g., about 5, 10, 25, 50, 75, 100, 125, or 150 mg/ml for antibody preparations.

In another aspect, the invention features an antibody purification method or an antibody preparation, wherein the amount of residual salt concentration bound to the antibody is less than that seen after the antibody has been exhaustively dialyzed, e.g., dialyzed in 0 mM salt.

In another aspect, the invention features a method of determining the propensity of a protein, e.g., an antibody, preparation, as described herein to have an opalescent appearance. The method includes: (i) (optionally) identifying a protein as having a tendency to self-aggregate, e.g., by determining the surface protein charge and/or second virial coefficient; and/or (ii) detecting formation and/or disappearance of high molecular weight species upon increasing and/or decreasing, respectively, the protein and/or salt concentration in one or more samples containing the protein in solution. A negative virial coefficient and/or an increase in high molecular weight species upon increasing salt and/or protein concentration are indicative of an increase propensity of the protein in the preparation to have an opalescent appearance.

In yet another aspect, the invention features a method of evaluating the opalescence of a protein, e.g., an antibody, sample. The method includes: providing a protein, e.g., an antibody, sample; determining the turbidity and/or presence of high molecular weight species at one or more (e.g., at least two, three or more) salt, e.g., NaCl, concentrations; providing a report on the level of opalescence in the protein, e.g., antibody, sample as a function of turbidity and/or presence of high molecular weight species at the one or more salt, e.g., NaCl, concentrations.

In other aspects, protein, e.g., antibody, preparations (as well as pharmaceutical compositions and/or formulations that include the protein preparations disclosed herein) having reduced opalescence are also within the scope of the invention. In embodiments, the protein preparations are produced by the methods described herein.

In other embodiments, the protein preparation includes at least 70%, 80%, 90%, 95%, 96%, 97%, 98%, 99% or higher percentage mass of non-aggregated species compared to the high molecular weight species (as detected, e.g., by dynamic light scattering) prior to removal of one or more high molecular weight species, e.g., a filtration or centrifugation step. In embodiments, a modification, e.g., a decrease, in the ionic strength of the protein preparation causes an increase of two-, three-, four-, five-, six-, seven-, eight-, nine-, ten-, fifty- or one hundred-fold in the percentage of non-aggregated protein compared to high molecular weight species.

In yet another aspect, the invention features a pharmaceutically acceptable antibody preparation that includes an antibody, e.g., a human or a humanized antibody, at a concentration of at least about 50, 75, 100, 125, or 150 mg/ml in less than about 50, 40, 30, 20, 10, 5, or 1 mM salt, e.g., NaCl.

In another aspect, the invention features a method of providing an antibody preparation that includes: (i) providing an antibody solution, e.g., of a human or humanized antibody having at least 70%, 80%, 90%, 95%, 96%, 97%, 98%, 99% or higher percentage mass of non-aggregated species prior to removal of one or more high molecular weight species, e.g., a filtration or centrifugation step; (ii) performing one or more purification steps to provide an intermediate antibody solution; and (iii) processing the intermediate solution to provide an antibody preparation having a concentration of at least about 50 to 150 mg/ml and a turbidity of less than about 5, 4, 3, 2, 1 or less European Pharmacopeia standard.

Other aspects, features and advantages will be apparent from the description of the preferred implementations thereof and from the claims.

DETAILED DESCRIPTION

The present application discloses methods of reducing the opalescent appearance of a protein preparation by modifying the ionic strength of the preparation, as well as compositions, e.g., pharmaceutical compositions, of concentrated protein with decreased opalescence are disclosed. Purification methods which monitor and/or reduce the salt concentrations at selected steps are also disclosed.

In one embodiment, the impact of salt concentration, i.e., ionic strength, on the opalescent appearance of concentrated antibody preparations was evaluated for three antibodies: Antibody M1 (also referred to herein as "Myo-029"), Antibody M2, and Antibody M3. As described in more detail in the appended Example, it was found that all three antibodies contain a relatively small amount of an extremely large species in just 10 mM histidine at pH 6.0. This large species was too large to be separated using an SEC-HPLC column. Increasing the ionic strength by increasing the amount of sodium chloride in the antibody preparation increases the opalescence, as well as the appearance of a liquid-liquid phase separation for Antibody M1 (see e.g., FIGS. 1-4). The opalescent appearance is reversible upon salt removal as shown for Antibody M1 in FIGS. 5-6. A large species was observed for Antibody M1 using asymmetric Flow Field Flow Fractionation (aFFFF), which was later confirmed using dynamic light scattering techniques (see FIG. 2). Although Antibodies M2 and M3 did not show a significant increase in opalescence detectable by visual inspection compared to Antibody M1 (see e.g., FIG. 7), high molecular weight species were detected for both antibodies using light scattering techniques (shown in FIGS. 8 and 9).

Figure 10:
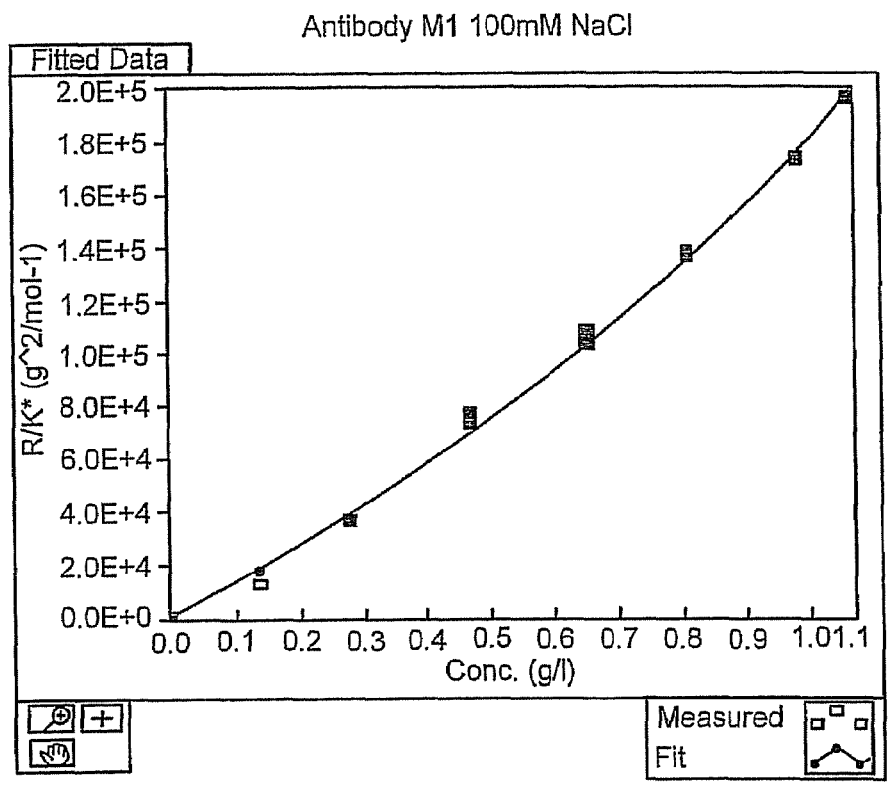
FIG. 10 shows a second virial coefficient plot for Antibody M1 at 100 mM NaCl.
Figure 11:
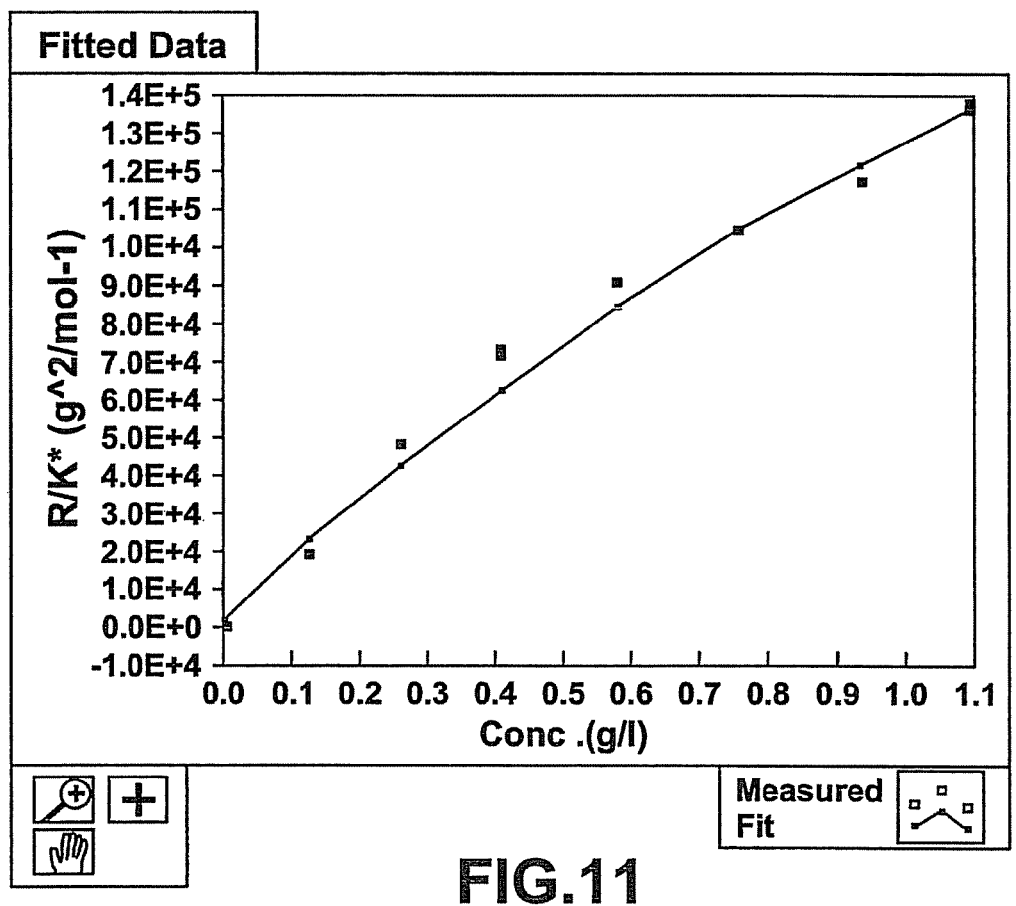
FIG. 11 shows a second virial coefficient plot for Antibody M2 at 100 mM NaCl.

A negative virial coefficient calculated for Antibody M1 is consistent with the aggregation/association tendencies of Antibody M1, as compared to Antibody M3 and Antibody M2 (both of which have a positive virial coefficient) (compare FIG. 10 with FIG. 11).

The results shown herein indicate that opalescent appearance of the antibodies studied is due primarily to reversible self-association, which is further induced by increasing ionic strength. Accordingly, as disclosed by the present invention, in order to reduce the opalescent appearance of concentrated antibody preparations (particularly those having a tendency to aggregate), the ionic strength of the antibody preparation should be decreased from the formulation and/or limited in the processing method.

In order that the present invention may be more readily understood, certain terms are first defined. Additional definitions are set forth throughout the detailed description.

The term "opalescence" or "opalescent appearance" refers to the degree of turbidity detected in a solution, e.g., a protein preparation, as a function of the concentration of one or more of the components in the solution, e.g., protein and/or salt concentration. The degree of turbidity can be calculated by reference to a standard curve generated using suspensions of known turbidity. Reference standards for determining the degree of turbidity for pharmaceutical compositions can be based on the European Pharmacopeia criteria (European Pharmacopoeia, Fourth Ed., Directorate for the Quality of Medicine of the Council of Europe (EDQM), Strasbourg, France). According to the European Pharmacopeia criteria, a clear solution is defined as one with a turbidity less than or equal to a reference suspension which has a turbidity of approximately 3 according to European Pharmacopeia standards. Nephelometric turbidity measurements can detect Rayleigh scatter, which typically changes linearly with concentration, in the absence of association or nonideality effects.

For example, ideal solutions behave consistently with the following formula:

$$KC/R_\theta = 1/M$$

where M is molecular weight, K is a constant, $R_\theta$ is the Rayleigh ratio (which combines a number of experimental parameters), and C is concentration. Whereas, non-ideal solutions can be described using the following formula:

$$KC/R_\theta = 1/M + 2BC + \ldots$$

where B is the second virial coefficient. To obtain M, $KC/R_\theta$ is extrapolated to zero angle and zero concentration. A Zimm plot places $KC/R_\theta$ on the ordinate and $\sin^2(\theta/2) + kC$ on the abscissa, where k is an arbitrary constant. The Zimm plot, thus, allows both $KC/R_\theta$ zero angle and zero concentration extrapolations to be made on the same graph. With the Zimm plot, M and B are respectively the intercept and slope of the zero angle line.

The term "second virial coefficient" is art-recognized to refer to a measure of the excluded volume effects and intermolecular interactions (Tessier, P. M. et al. (2003) *Current Opinion in Biotechnology* 14(5):512-516). A positive second virial coefficient is typically indicative of both excluded volume effects and intermolecular repulsive interactions. In contrast, a negative second virial coefficient typically indicates attractive intermolecular interactions. The balance of these intra- and intermolecular interactions determine the sign and amplitude of the second virial coefficient.

The term "ionic strength" refers to the concentration of ions in a solution. If "I" is ionic strength:

$$I = \frac{1}{2}\sum_{i=1}^{n} c_i z_i^2$$

where $c_i$ is the molarity concentration of ion i, $z_i$ is the charge of that ion, and the sum is taken over all ions in the solution. (IUPAC Compendium of Chemical Terminology, 2nd Ed. (1997)).

The term "protein" as used herein refers to one or more polypeptides that can function as a unit. The term "polypeptide" as used herein refers a sequential chain of amino acids linked together via peptide bonds. The term "polypeptide" is used to refer to an amino acid chain of any length, but one of ordinary skill in the art will understand that the term is not limited to lengthy chains and can refer to a minimal chain comprising two amino acids linked together via a peptide bond. If a single polypeptide can function as a unit, the terms "polypeptide" and "protein" may be used interchangeably. The terms proteins and polypeptides include antibodies, receptor fusions, SMIP™, growth factors, cytokines, clotting factors and enzymes, as described in more detail below.

The term "antibody" refers to any immunoglobulin or fragment thereof, and encompasses any peptide or polypeptide comprising an antigen-binding site. The term includes, but is not limited to, polyclonal, monoclonal, monospecific, polyspecific, bi-specific, humanized, de-immunized, human, camelid, rodent, single-chain, chimeric, synthetic, recombinant, hybrid, mutated, grafted, and in vitro generated antibodies. The term "antibody" also includes antibody fragments and variant molecules such as Fab, F(ab')$_2$, Fv, scFv, Fd, dAb, VHH, and other antibody fragments and variant molecules that retain antigen-binding function. Typically, such fragments would comprise an antigen-binding domain.

The term "protein preparation" refers to any composition containing at least one protein, e.g., an antibody, in solution, which is capable of forming high molecular weight species upon an increase in the ionic strength of the preparation. The protein preparation may contain the same or different proteins, e.g., antibodies having different binding specificity.

The term "high molecular weight species" refers to an association of at least two proteins, e.g., antibodies. In embodiments, the protein association leads to the formation of higher order aggregates of monomeric protein. The association may arise as a result of non-covalent (e.g., electrostatic, van der Waals) protein-protein interactions. The association is typically reversible upon reducing the ionic strength of the protein preparation. The proteins may be the same or different, e.g., antibodies having different binding specificity. The high molecular weight species typically have a molecular weight of about $10^4$, more typically, about $10^5$, $10^6$, $10^7$, $10^8$, $10^9$, $10^{10}$, $10^{11}$, $10^{12}$, $10^{13}$, or higher.

The aggregation of proteins to form high molecular weight species can be monitored using several analytical techniques, including, but not limited to, optical density, asymmetric flow field flow fractionation, SEC-HPLC, static light scattering, and dynamic light scattering, as described in more detail herein.

Turbidity of a protein sample can be measured as optical density (absorbance of light at a specific wavelength). An optical density measurement can be made using spectrophotometry (e.g., using a SpectraMax UV-Vis at a wavelength of 400 nm). For a more detailed description of how to measure optical density, see e.g., Eckhardt B M (1994) *J Pharm Sci Technol*. 48(2):64-70.

Asymmetric flow field flow fractionation (AF4) is a type of asymmetric field flow fractionation. AF4 is a method capable of rapid fractionation and high resolution characterization of various particles including bio-molecules (Giddings, J. C.; Yang, F. J.; Myers, M. N., *Flow-field-flow fractionation: a versatile new separation method,* 193 Science 1244-1245 (1976); Giddings, J. C.; Yang, F. J.; Myers, M. N., *Theoretical and experimental characterization of flow field-flow fractionation,* 48 Anal. Chem. 1126-1132 (1976)). AF4 is capable of separating particles ranging from a few nanometers to a few micrometers. Field flow fractionation separation occurs in a thin flow channel (comparable to a chromatographic separation column). An aqueous or organic solvent carries the sample through this channel. The flow through the channel, the first force exerted on the sample, is laminar due to the low channel height. A second force is generated perpendicular to the channel flow. In AF4, one side of the flow channel is a membrane and the second force is fluid flow across the channel through the membrane. Particle separation occurs in this system as a result of these two forces. First, the velocity gradient due to the laminar flow within the channel causes particles in the center of the channel to move more quickly along the channel and be separated from those closer to the sides of the channel. Second, the second force forces the sample toward the membrane. Size separation occurs because the smaller molecules diffuse back toward the center of the channel more quickly than larger particles and hence are separated from the larger particles due to the quicker solvent flow toward the center of the channel.

The acronym SEC-HPLC stands for size exclusion chromatography-high performance liquid chromatography. SEC and HPLC are individually well known analytical techniques as is the combination SEC-HPLC analytical technique. (Gamick, R. L., Ross, M. J., Du Mee, C. P., *Encyclopedia of pharmaceutical Technology*, Ed. J. Swarbrick, J. C., Boylan, Vol. 1: 253 (Marcel Dekker, Inc., New York, 1988)). Without delving into the theories behind each technique, SEC, also know as gel permeation chromatography, separates molecules based on size due to the molecules' ability to move through a gel matrix, and HPLC separates molecules based on diffusion coefficients as the molecules are moved past a stationary medium under high pressure.

Static and dynamic light scattering are two different experimental methods for measuring the patterns of light scattered from a solvent/solute system. (Berne, B. and Pecora, R. *Dynamic Light Scattering with Applications to Chemistry, Biology and Physics* (Wiley, New York, 1976)). Static and dynamic light scattering give complementary pieces of information, and for this reason they are commonly used in tandem for characterization of solutions.

Static light scattering involves measuring the angular dependency of the time-mean-intensity of laser light scattered by the particles in solution. The size and structure of the particles impact the light scatter intensity as a function of the detector angle. It has been well established that in the limit of low scatter vectors and low concentrations, the angular distribution of the scattered intensity becomes independent of the particle shape. (Zimm, B., *The scattering of light and the radial distribution function of high polymer solutions*, 16 *J. Chem. Phys.* 1093-9 (1948)). As discussed above, by extrapolation of ($Kc/R_\theta$) to zero angle and zero concentration, several factors including the average molecular weight, radius of gyration and second virial constant can be estimated.

Dynamic light scattering involves measuring the time-dependent fluctuations in the intensity of scattered light that occurs because the particles in solution, in this case proteins, are undergoing random, Brownian motion. By analyzing these intensity fluctuations, the distribution of diffusion coefficients of the particles can be determined. The distribution of diffusion coefficients can then be converted into a size distribution using well known theories. The upper sized limit for dynamic light scattering is sample density dependent, i.e., the particles must be able to move, so the upper limit is often the point at which the sedimentation of particles dominates the diffusion process. The lower limit will depend on the excess scattered light the sample generates compared to the suspending medium, as well as other factors including sample concentration, relative refractive indices, laser power, laser wavelength, detector sensitivity, etc.

Proteins

In certain embodiments, the proteins in the protein preparations are produced recombinantly. The terms "recombinantly expressed protein" and "recombinant protein" as used herein refer to a polypeptide expressed from a host cell that has been manipulated by the hand of man to express that polypeptide. In certain embodiments, the host cell is a mammalian cell. In certain embodiments, this manipulation may comprise one or more genetic modifications. For example, the host cells may be genetically modified by the introduction of one or more heterologous genes encoding the polypeptide to be expressed. The heterologous recombinantly expressed polypeptide can be identical or similar to polypeptides that are normally expressed in the host cell. The heterologous recombinantly expressed polypeptide can also be foreign to the host cell, e.g., heterologous to polypeptides normally expressed in the host cell. In certain embodiments, the heterologous recombinantly expressed polypeptide is chimeric. For example, portions of a polypeptide may contain amino acid sequences that are identical or similar to polypeptides normally expressed in the host cell, while other portions contain amino acid sequences that are foreign to the host cell. Additionally or alternatively, a polypeptide may contain amino acid sequences from two or more different polypeptides that are both normally expressed in the host cell. Furthermore, a polypeptide may contain amino acid sequences from two or more polypeptides that are both foreign to the host cell. In some embodiments, the host cell is genetically modified by the activation or upregulation of one or more endogenous genes.

Any protein showing an undesirable degree of opalescence and/or forming high molecular weight species can be used in accordance with the present invention. For example, the present invention may be employed to reduce the opalescence of any pharmaceutically or commercially relevant antibody, receptor, cytokine, growth factor, enzyme, clotting factor, hormone, regulatory factor, antigen, binding agent, among others. The following list of proteins that can be separated according to the present invention is merely exemplary in nature, and is not intended to be a limiting recitation. One of ordinary skill in the art will understand that any protein may be expressed in accordance with the present invention and will be able to select the particular protein to be produced based as needed.

Antibodies and Binding Fragments

Antibodies, also known as immunoglobulins, are typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain includes an N-terminal variable (V) domain (VL) and a constant (C) domain (CL). Each heavy chain includes an N-terminal V domain (VH), three or four C domains (CHs), and a hinge region. The CH domain most proximal to VH is designated as CH1. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see *Antibodies: A Laboratory Manual, Cold Spring Harbor Laboratory*, eds. Harlow et al., 1988. One of skill in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in *Sequences of proteins of Immunological Interest, US Department of Health and Human Services* (1991), eds. Kabat et al. Another standard for characterizing the antigen binding site is to refer to the hypervariable loops as described by Chothia. See, e.g., Chothia, D. et al. (1992) *J. Mol. Biol.* 227:799-817; and Tomlinson et al. (1995) *EMBO J.* 14:4628-4638. Still another standard is the AbM definition used by Oxford Molecular's AbM antibody modelling software. See, generally, e.g., *Protein Sequence and Structure Analysis of Antibody Variable Domains*. In: *Antibody Engineering Lab Manual* (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops.

Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; (vi) a camelid or camelized variable domain, e.g., a VHH domain; (vii) a single chain Fv (scFv); and (viii) a bispecific antibody. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) *Science* 242:423-26; Huston et al. (1988) *Proc. Natl. Acad. Sci. U.S.A.* 85:5879-83). Such single chain antibodies are also intended to be encompassed within the term "antigen-binding fragment" of an antibody. These antibody fragments are obtained using conventional techniques known to those skilled in the art, and the fragments are evaluated for function in the same manner as are intact antibodies.

Other than "bispecific" or "bifunctional" antibodies, an antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

Numerous methods known to those skilled in the art are available for obtaining antibodies. For example, monoclonal antibodies may be produced by generation of hybridomas in accordance with known methods. Hybridomas formed in this manner are then screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies includes screening protein expression libraries, e.g., phage or ribosome display libraries. Phage display is described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; and WO 90/02809.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nature Genetics* 7:13-21, US 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See e.g., Morrison et al., *Proc. Natl. Acad. Sci. U.S.A.* 81:6851, 1985; Takeda et al., *Nature* 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies can be generated by replacing sequences of the Fv variable domain that are not directly involved in antigen binding with equivalent sequences from human Fv variable domains. Exemplary methods for generating humanized antibodies or fragments thereof are provided by Morrison (1985) *Science* 229:1202-1207; by Oi et al. (1986) *BioTechniques* 4:214; and by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., *Proc. Natl. Acad. Sci. U.S.A.,* 80: 7308-7312, 1983; Kozbor et al., *Immunology Today,* 4: 7279, 1983; Olsson et al., *Meth. Enzymol.,* 92: 3-16, 1982), and may be made according to the teachings of PCT Publication WO92/06193 or EP 0239400).

An antibody may also be modified by specific deletion of human T cell epitopes or "deimmunization" by the methods disclosed in WO 98/52976 and WO 00/34317. Briefly, the heavy and light chain variable domains of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et al. (1992) *J. Mol. Biol.* 227:776-798; Cook, G. P. et al. (1995) *Immunol. Today Vol.* 16 (5): 237-242; Chothia, D. et al. (1992) *J. Mol. Biol.* 227:799-817; and Tomlinson et al. (1995) *EMBO J.* 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

In certain embodiments, an antibody can contain an altered immunoglobulin constant or Fc region. For example, an antibody produced in accordance with the teachings herein may bind more strongly or with more specificity to effector molecules such as complement and/or Fc receptors, which can control several immune functions of the antibody such as effector cell activity, lysis, complement-mediated activity, antibody clearance, and antibody half-life. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, *Annu. Rev. Immunol* 9:457-92, 1991; Capel et al., *Immunomethods* 4:25-34, 1994; and de Haas et al., *J. Lab. Clin. Med.* 126:330-41, 1995).

Non-limiting examples of antibodies that can be separated by the methods of the invention, include but are not limited to, antibodies against Aβ, IL-13, IL-22, GDF8 and 5T4. Each of these antibodies is described in more detail hereinbelow and the appended Examples.

Anti-GDF8 Antibodies

Exemplary antibodies that can be used in the methods of the invention are anti-GDF8 antibodies. The term "GDF-8" refers to growth and differentiation factor-8 and, where appropriate, factors that are structurally or functionally related to GDF-8, for example, BMP-11 and other factors belonging to the TGF-β superfamily. The term refers to the full-length unprocessed precursor form of GDF-8, as well as the mature and propeptide forms resulting from post-translational cleavage. The term also refers to any fragments and variants of GDF-8 that maintain at least some biological activities associated with mature GDF-8, including sequences that have been modified. The amino acid sequence human GDF-8, as well as many other vertebrate species (including murine, baboon, bovine, chicken) is disclosed, e.g., US 2004/0142382, US 2002/0157125, and McPherron et al. (1997) Proc. Nat. Acad. Sci. U.S.A., 94:12457-12461). Examples of neutralizing antibodies against GDF-8, e.g., Myo-029, are disclosed in, e.g., U.S. 2004/0142382, and are referenced throughout the Examples appended herein. Exemplary disease and disorders include muscle and neuromuscular disorders such as muscular dystrophy (including Duchenne's muscular dystrophy); amyotrophic lateral sclerosis; muscle atrophy; organ atrophy; frailty; tunnel syndrome; congestive obstructive pulmonary disease; sarcopenia, cachexia, and other muscle wasting syndromes; adipose tissue disorders (e.g., obesity); type 2 diabetes; impaired glucose tolerance; metabolic syndromes (e.g., syndrome X); insulin resistance induced by trauma such as burns or nitrogen imbalance; and bone degenerative diseases (e.g., osteoarthritis and osteoporosis).

Anti-Aβ Antibodies

A reduction in the opalescence of anti-Aβ antibody preparations can be practiced following the teachings of the invention. The terms "AB antibody," "Aβ antibody," "anti-Aβ antibody," and "anti-Aβ" are used interchangeably herein to refer to an antibody that binds to one or more epitopes or antigenic determinants of APP, Aβ protein, or both. Exemplary epitopes or antigenic determinants can be found within the human amyloid precursor protein (APP), but are preferably found within the Aβ peptide of APP. Multiple isoforms of APP exist, for example APP$^{695}$, APP$^{751}$, and APP$^{770}$. Amino acids within APP are assigned numbers according to the sequence of the APP$^{770}$ isoform (see e.g., GenBank Accession No. P05067). Aβ (also referred to herein as beta amyloid peptide and A beta) peptide is a ~4-kDa internal fragment of 39-43 amino acids of APP (Aβ39, Aβ40, Aβ041, Aβ042, and Aβ43). Aβ40, for example, consists of residues 672-711 of APP and Aβ42 consists of residues 672-713 of APP. As a result of proteolytic processing of APP by different secretase enzymes iv vivo or in situ, Aβ is found in both a "short form," 40 amino acids in length, and a "long form," ranging from 42-43 amino acids in length. Epitopes or antigenic determinants can be located within the N-terminus of the Aβ peptide and include residues within amino acids 1-10 of Aβ, preferably from residues 1-3, 1-4, 1-5, 1-6, 1-7, 2-7, 3-6, or 3-7 of Aβ42 or within residues 2-4, 5, 6, 7, or 8 of Aβ, residues 3-5, 6, 7, 8, or 9 of Aβ, or residues 4-7, 8, 9, or 10 of Aβ42. "Central" epitopes or antigenic determinants are located within the central or mid-portion of the Aβ peptide and include residues within amino acids 16-24, 16-23, 16-22, 16-21, 19-21, 19-22, 19-23, or 19-24 of Aβ. "C-terminal" epitopes or antigenic determinants are located within the C-terminus of the Aβ peptide and include residues within amino acids 33-40, 33-41, or 33-42 of Aβ.

In various embodiments, an Aβ antibody is end-specific. As used herein, the term "end-specific" refers to an antibody which specifically binds to the N-terminal or C-terminal residues of an Aβ peptide but that does not recognize the same residues when present in a longer Aβ species comprising the residues or in APP.

In various embodiments, an Aβ antibody is "C-terminus-specific." As used herein, the term "C terminus-specific" means that the antibody specifically recognizes a free C-terminus of an Aβ peptide. Examples of C terminus-specific Aβ antibodies include those that: recognize an Aβ peptide ending at residue 40, but do not recognize an Aβ peptide ending at residue 41, 42, and/or 43; recognize an Aβ peptide ending at residue 42, but do not recognize an Aβ peptide ending at residue 40, 41, and/or 43; etc.

In one embodiment, the antibody may be a 3D6 antibody or variant thereof, or a 10D5 antibody or variant thereof, both of which are described in U.S. Patent Publication No. 2003/0165496A1, U.S. Patent Publication No. 2004/0087777A1, International Patent Publication No. WO02/46237A3. Description of 3D6 and 10D5 can also be found, for example, in International Patent Publication No. WO02/088306A2 and International Patent Publication No. WO02/088307A2. 3D6 is a monoclonal antibody (mAb) that specifically binds to an N-terminal epitope located in the human β-amyloid peptide, specifically, residues 1-5. By comparison, 10D5 is a mAb that specifically binds to an N-terminal epitope located in the human β-amyloid peptide, specifically, residues 3-6. In another embodiment, the antibody may be a 12B4 antibody or variant thereof, as described in U.S. Patent Publication No. 20040082762A1 and International Patent Publication No. WO03/077858A2. 12B4 is a mAb that specifically binds to an N-terminal epitope located in the human β-amyloid peptide, specifically, residues 3-7. In yet another embodiment, the antibody may be a 12A11 antibody or a variant thereof, as described in U.S. patent application Ser. No. 10/858,855 and International Patent Application No. PCT/US04/17514. 12A11 is a mAb that specifically binds to an N-terminal epitope located in the human β-amyloid peptide, specifically, residues 3-7. In yet another embodiment, the antibody may be a 266 antibody as described in U.S. patent application Ser. No. 10/789,273, and International Patent Application No. WO01/62801A2. Antibodies designed to specifically bind to C-terminal epitopes located in human β-amyloid peptide, for use in the present invention include, but are not limited to, 369.2B, as described in U.S. Pat. No. 5,786,160.

In exemplary embodiments, the antibody is a humanized anti Aβ peptide 3D6 antibody that selectively binds Aβ peptide. More specifically, the humanized anti Aβ peptide 3D6 antibody is designed to specifically bind to an NH$_2$-terminal epitope located in the human β-amyloid 1-40 or 1-42 peptide found in plaque deposits in the brain (e.g., in patients suffering from Alzheimer's disease).

Anti-Aβ antibodies can be used to treat amyloidogenic diseases, in particular, Alzheimer's Disease. The term "amyloidogenic disease" includes any disease associated with (or caused by) the formation or deposition of insoluble amyloid fibrils. Exemplary amyloidogenic diseases include, but are not limited to, systemic amyloidosis, Alzheimer's disease, mature onset diabetes, Parkinson's disease, Huntington's disease, fronto-temporal dementia, and the prion-related transmissible spongiform encephalopathies (kuru and Creutzfeldt-Jacob disease in humans and scrapie and BSE in sheep and cattle, respectively). Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit. Accordingly, Alzheimer's disease is an example of a "disease characterized by deposits of Aβ" or a "disease associated with deposits of Aβ," e.g., in the brain of a subject or patient. The terms "β-amyloid protein," "β-amyloid peptide," "β-amyloid," "Aβ," and "Aβ peptide" are used interchangeably herein.

Anti-5T4 Antibodies

The 5T4 antigen has been previously characterized (see e.g., WO 89/07947). The full nucleic acid sequence of human 5T4 is known (Myers et al. (1994) *J Biol Chem* 169: 9319-24 and GenBank at Accession No. Z29083). The sequence for 5T4 antigen from other species is also known, for example, murine 5T4 (WO00/29428), canine 5T4 (WO01/36486) or feline 5T4 (U.S. Ser No. 05/0100958).

Human 5T4 is a glycoprotein of about 72 kDa expressed widely in carcinomas, but having a highly restricted expression pattern in normal adult tissues. It appears to be strongly correlated to metastasis in colorectal and gastric cancer. Expression of the 5T4 antigen is also found at high frequency in breast and ovarian cancers (Starzynska et al. (1998) *Eur. J. Gastroenterol. Hepatol.* 10:479-84; Starzynska et al. (1994) *Br. J. Cancer* 69:899-902; Starzynska et al. (1992) *Br. J. Cancer* 66:867-9). 5T4 has been proposed as a marker, with possible mechanistic involvement, for tumor progression and metastasis potential (Carsberg et al. (1996) *Int J Cancer* 68:84-92). 5T4 has also been proposed for use as an immunotherapeutic agent (see WO 00/29428). Antigenic peptides of 5T4 are disclosed in, e.g., U.S. Ser No. 05/0100958, the contents of which are incorporated by reference.

Several pending applications relate generally to nucleic acids encoding the anti-5T4 monoclonal antibody, vectors and host cells thereof, for example, U.S. Application Publication Nos. 2003/0018004 and 2005/0032216. A provisional patent application pertaining generally to the humanized anti-5T4H8 monoclonal antibodies and calicheamicin conjugates thereof, as well as methods of treatment using these calicheamicin conjugates has been filed (U.S. Application Publication No. 2006/0088522). The contents of all of these applications are incorporated by reference herein in their entirety.

Anti-IL13 Antibodies

Interleukin-13 (IL-13) is a previously characterized cytokine secreted by T lymphocytes and mast cells (McKenzie et al. (1993) *Proc. Natl. Acad. Sci. USA* 90:3735-39; Bost et al. (1996) *Immunology* 87:663-41). The term "IL-13" refers to interleukin-13, including full-length unprocessed precursor form of IL-13, as well as the mature forms resulting from post-translational cleavage. The term also refers to any fragments and variants of IL-13 that maintain at least some biological activities associated with mature IL-13, including sequences that have been modified. The term "IL-13" includes human IL-13, as well as other vertebrate species. Several pending applications disclose antibodies against human and monkey IL-13, IL-13 peptides, vectors and host cells producing the same, for example, U.S. Application Publication Nos. 2006/0063228A and 2006/0073148. The contents of all of these publications are incorporated by reference herein in their entirety.

IL-13 shares several biological activities with IL-4. For example, either IL-4 or IL-13 can cause IgE isotype switching in B cells (Tomkinson et al. (2001) *J. Immunol.* 166:5792-5800). Additionally, increased levels of cell surface CD23 and serum CD23 (sCD23) have been reported in asthmatic patients (Sanchez-Guererro et al. (1994) *Allergy* 49:587-92; DiLorenzo et al. (1999) *Allergy Asthma Proc.* 20:119-25). In addition, either IL-4 or IL-13 can upregulate the expression of MHC class II and the low-affinity IgE receptor (CD23) on B cells and monocytes, which results in enhanced antigen presentation and regulated macrophage function (Tomkinson et al., supra). These observations suggest that IL-13 may be an important player in the development of airway eosinophilia and airway hyperresponsiveness (AHR) (Tomkinson et al., supra; Wills-Karp et al. (1998) *Science* 282:2258-61). Accordingly, inhibition of IL-13 can be useful in ameliorating the pathology of a number of inflammatory and/or allergic conditions, including, but not limited to, respiratory disorders, e.g., asthma; chronic obstructive pulmonary disease (COPD); other conditions involving airway inflammation, eosinophilia, fibrosis and excess mucus production, e.g., cystic fibrosis and pulmonary fibrosis; atopic disorders, e.g., atopic dermatitis, urticaria, eczema, allergic rhinitis; inflammatory and/or autoimmune conditions of, the skin (e.g., atopic dermatitis), gastrointestinal organs (e.g., inflammatory bowel diseases (IBD), such as ulcerative colitis and/or Crohn's disease), liver (e.g., cirrhosis, hepatocellular carcinoma); scleroderma; tumors or cancers (e.g., soft tissue or solid tumors), such as leukemia, glioblastoma, and lymphoma, e.g., Hodgkin's lymphoma; viral infections (e.g., from HTLV-1); fibrosis of other organs, e.g., fibrosis of the liver, (e.g., fibrosis caused by a hepatitis B and/or C virus).

Anti-IL22 Antibodies

Interleukin-22 (IL-22) is a previously characterized class II cytokine that shows sequence homology to IL-10. Its expression is up-regulated in T cells by IL-9 or ConA (Dumoutier L. et al. (2000) *Proc Natl Acad Sci USA* 97(18):10144-9). Studies have shown that expression of IL-22 mRNA is induced in vivo in response to LPS administration, and that IL-22 modulates parameters indicative of an acute phase response (Dumoutier L. et al. (2000) supra; Pittman D. et al. (2001) *Genes and Immunity* 2:172), and that a reduction of IL-22 activity by using a neutralizing anti-IL-22 antibody ameliorates inflammatory symptoms in a mouse collagen-induced arthritis (CIA) model. Thus, IL-22 antagonists, e.g., neutralizing anti-IL-22 antibodies and fragments thereof, can be used to induce immune suppression in vivo, for examples, for treating autoimmune disorders (e.g., arthritic disorders such as rheumatoid arthritis); respiratory disorders (e.g., asthma, chronic obstructive pulmonary disease (COPD)); inflammatory conditions of, e.g., the skin (e.g., psoriasis), cardiovascular system (e.g., atherosclerosis), nervous system (e.g., Alzheimer's disease), kidneys (e.g., nephritis), liver (e.g., hepatitis) and pancreas (e.g., pancreatitis).

The term "IL-22" refers to interleukin-22, including full-length unprocessed precursor form of IL-22, as well as the mature forms resulting from post-translational cleavage. The term also refers to any fragments and variants of IL-22 that maintain at least some biological activities associated with mature IL-22, including sequences that have been modified. The term "IL-22" includes human IL-22, as well as other vertebrate species. The amino acid and nucleotide sequences of human and rodent IL-22, as well as antibodies against IL-22 are disclosed in, for example, U.S. Application Publication Nos. 2005-0042220 and 2005-0158760, and U.S. Pat. No. 6,939,545. The contents of all of these publications are incorporated by reference herein in their entirety.

Small Modular ImmunoPharmaceuticals (SMIP™)

The present invention can also be applied to Small Modular ImmunoPharmaceuticals (SMIP™). It typically refers to a binding domain-fusion protein that includes a binding domain polypeptide that is fused or otherwise connected to an immunoglobulin hinge or hinge-acting region polypeptide, which in turn is fused or otherwise connected to a region comprising one or more native or engineered constant regions from an immunoglobulin heavy chain, other than CH1, for example, the CH2 and CH3 regions of IgG and IgA, or the CH3 and CH4 regions of IgE (see e.g., U.S. 05/0136049 by Ledbetter, J. et al. for a more, complete description). The binding domain-immunoglobulin fusion protein can further include a region that includes a native or engineered immunoglobulin heavy chain CH2 constant region polypeptide (or CH3 in the case of a construct derived in whole or in part from IgE) that is fused or otherwise connected to the hinge region polypeptide and a native or engineered immunoglobulin heavy chain CH3 constant region polypeptide (or CH4 in the case of a construct derived in whole or in part from IgE) that is fused or otherwise connected to the CH2 constant region polypeptide (or CH3 in the case of a construct derived in whole or in part from IgE). Typically, such binding domain-immunoglobulin fusion proteins are capable of at least one immunological activity selected from the group consisting of antibody dependent cell-mediated cytotoxicity, complement fixation, and/or binding to a target, for example, a target antigen.

Soluble Receptors and Receptor Fusions

The invention can also be applied to soluble receptors or fragments thereof. Examples of soluble receptors include the extracellular domain of a receptor, such as soluble tumor necrosis factor alpha and beta receptors (TNFR-1; EP 417,563 published Mar. 20, 1991; TNFR-2, EP 417,014 published Mar. 20, 1991; and reviewed in Naismith and Sprang, *J Inflamm.* 47(1-2): 1-7, 1995-96, each of which is incorporated herein by reference in its entirety). In other embodiments, the soluble receptor includes the extracellular domain of interleukin-21 receptor (IL-21R) as described in, for example, US 2003-0108549 (the contents of which are also incorporated by reference).

The fusion protein can include a targeting moiety, e.g., a soluble receptor fragment or a ligand, and an immunoglobulin chain, an Fc fragment, a heavy chain constant regions of the various isotypes, including: IgG1, IgG2, IgG3, IgG4, IgM, IgA1, IgA2, IgD, and IgE. For example, the fusion protein can include the extracellular domain of a receptor, and, e.g., fused to, a human immunoglobulin Fc chain (e.g., human IgG, e.g., human IgG1 or human IgG4, or a mutated form thereof). In one embodiment, the human Fc sequence has been mutated at one or more amino acids, e.g., mutated at residues 254 and 257 from the wild type sequence to reduce Fc receptor binding. The fusion proteins may additionally include a linker sequence joining the first moiety to the second moiety, e.g., the immunoglobulin fragment. For example, the fusion protein can include a peptide linker, e.g., a peptide linker of about 4 to 20, more preferably, 5 to 10, amino acids in length; the peptide linker is 8 amino acids in length. For example, the fusion protein can include a peptide linker having the formula (Ser-Gly-Gly-Gly-Gly)y wherein y is 1, 2, 3, 4, 5, 6, 7, or 8. In other embodiments, additional amino acid sequences can be added to the N- or C-terminus of the fusion protein to facilitate expression, steric flexibility, detection and/or isolation or purification.

In certain embodiments, the soluble receptor fusion comprises a soluble TNFR-Ig (e.g., a soluble fragment of a TNF receptor, e.g., p55 or p75 human TNF receptor or derivatives thereof, e.g., 75 kd TNFR-IgG (e.g., 75 kD TNF receptor fused to a 235 amino acid Fc portion of human IgG1).

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) *Current Protocols in Molecular Biology*, John Wiley & Sons, 1992). Moreover, many expression vectors are commercially available that encode a fusion moiety (e.g., an Fc region of an immunoglobulin heavy chain). Immunoglobulin fusion polypeptides are known in the art and are described in e.g., U.S. Pat. Nos. 5,516,964; 5,225,538; 5,428,130; 5,514,582; 5,714,147; and 5,455,165.

Growth Factors and Cytokines

Another class of polypeptides that have been shown to be effective as pharmaceutical and/or commercial agents and that can desirably be produced according to the teachings of the present invention includes growth factors and other signaling molecules, such as cytokines.

Growth factors are typically glycoproteins that are secreted by cells and bind to and activate receptors on other cells, initiating a metabolic or developmental change in the receptor cell. Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (TLs), e.g., IL-1 to IL-13 (e.g., IL-11); tumor necrosis factor (TNF) alpha and beta; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; prorelaxin; mouse gonadotropin-associated peptide; neurotrophic factors such as bone-derived neurotrophic factor (BDNF), neurotrophin-3, -4, -5, or -6 (NT-3, NT-4, NT-5, or NT-6), or a nerve growth factor such as NGF-beta. One of ordinary skill in the art will be aware of other growth factors or signaling molecules that can be expressed in accordance with methods and compositions of the present invention.

Specific alterations in the glycosylation pattern of growth factors or other signaling molecules have been shown to have dramatic effects on their therapeutic properties. As one example, a common method of treatment for patients who suffer from chronic anemia is to provide them with frequent injections of recombinant human erythropopietin (rHuEPO) in order to boost their production of red blood cells. An analog of rHuEPO, darbepoetin alfa (ARANESP®), has been developed to have a longer duration than normal rHuEPO. The primary difference between darbepoetin alfa and rHuEPO is the presence of two extra sialic-acid-containing N-linked oligosaccharide chains. Production of darbepoetin alfa has been accomplished using in vitro glycoengineering (see Elliott et al., *Nature Biotechnology* 21(4):414-21, 2003, incorporated herein by reference in its entirety). Elliott et al. used in vitro mutagenesis to incorporate extra glycosylation sites into the rHuEPO polypeptide backbone, resulting in expression of the darbepoetin alfa analog. The extra oligosaccharide chains are located distal to the EPO receptor binding site and apparently do not interfere with receptor binding. However, darbepoetin alfa's half-life is up to three-fold higher than rHuEPO, resulting in a much more effective therapeutic agent.

Clotting Factors

Clotting factors have been shown to be effective as pharmaceutical and/or commercial agents. Hemophilia B is a disorder in which the blood of the sufferer is unable to clot. Thus, any small wound that results in bleeding is potentially a life-threatening event. For example, Coagulation Factor IX (Factor 1× or "FIX") is a single-chain glycoprotein whose deficiency results in Hemophilia B. FIX is synthesized as a single chain zymogen that can be activated to a two-chain serine protease (Factor IXa) by release of an activation peptide. The catalytic domain of Factor IXa is located in the heavy chain (see Chang et al., *J. Clin. Invest.*, 100:4, 1997, incorporated herein by reference in its entirety). FIX has multiple glycosylation sites including both N-linked and O-linked carbohydrates. One particular O-linked structure at Serine 61 (Sia-α2,3-Gal-β1,4-GlcNAc-β1,3-Fuc-α1-O-Ser) was once thought unique to FIX but has since found on a few other molecules including the Notch protein in mammals and *Drosophila* (Maloney et al, *Journal of Biol. Chem.*, 275(13), 2000). FIX produced by Chinese Hamster Ovary ("CHO") cells in cell culture exhibits some variability in the Serine 61 oligosaccharide chain. These different glycoforms, and other potential glycoforms, may have different abilities to induce clotting when administered to humans or animals and/or may have different stabilities in the blood, resulting in less effective clotting.

Hemophilia A, which is clinically indistinguishable from Hemophilia B, is caused by a defect in human clotting factor VIII, another glycoprotein that is synthesized as a single chain and then processed into a two-chain active form. The present invention may also be employed to control or alter the glycosylation pattern of clotting factor VIII in order to modulate its clotting activity. Other clotting factors that can be produced in accordance with the present invention include tissue factor and von Willebrands factor.

Enzymes

Another class of polypeptides that have been shown to be effective as pharmaceutical and/or commercial agents and that can desirably be produced according to the teachings of the present invention includes enzymes. Enzymes may be glycoproteins whose glycosylation pattern affects enzymatic activity. Thus, the present invention may also be used to produce enzymes in a cell culture wherein the produced enzymes have a more extensive or otherwise more desirable glycosylation pattern.

As but one non-limiting example, a deficiency in glucocerebrosidase (GCR) results in a condition known as Gaucher's disease, which is caused by an accumulation of glucocerebrosidase in lysosomes of certain cells. Subjects with Gaucher's disease exhibit a range of symptoms including splenomegaly, hepatomegaly, skeletal disorder, thrombocytopenia and anemia. Friedman and Hayes showed that recombinant GCR (rGCR) containing a single substitution in the primary amino acid sequence exhibited an altered glycosylation pattern, specifically an increase in fucose and N-acetyl glucosamine residues compared to naturally occurring GCR (see U.S. Pat. No. 5,549,892).

Friedman and Hayes also demonstrated that this rGCR exhibited improved pharmacokinetic properties compared to naturally occurring rGCR. For example, approximately twice as much rGCR targeted liver Kupffer cells than did naturally occurring GCR. Although the primary amino acid sequences of the two proteins differed at a single residue, Friedman and Hayes hypothesized that the altered glycosylation pattern of rGCR may also influence the targeting to Kupffer cells. One of ordinary skill in the art will be aware of other known examples of enzymes that exhibit altered enzymatic, pharmacokinetic and/or pharmacodynamic properties resulting from an alteration in their glycosylation patterns.

Protein Production

Recombinant methods of producing the proteins according to the invention are known in the art. Nucleotide sequences encoding the proteins are typically inserted in an expression vector for introduction into host cells that may be used to produce the desired quantity of modified antibody that, in turn, provides the polypeptides. The term "vector" includes a nucleic acid construct often including a nucleic acid, e.g., a gene, and further including minimal elements necessary for nucleic acid replication, transcription, stability and/or protein expression or secretion from a host cell. Such constructs may exist as extrachromosomal elements or may be integrated into the genome of a host cell.

The term "expression vector" includes a specific type of vector wherein the nucleic acid construct is optimized for the high-level expression of a desired protein product. Expression vectors often have transcriptional regulatory agents, such as promoter and enhancer elements, optimized for high-levels of transcription in specific cell types and/or optimized such that expression is constitutive based upon the use of a specific inducing agent. Expression vectors further have sequences that provide for proper and/or enhanced translation of the protein As known to those skilled in the art, such vectors may easily be selected from the group consisting of plasmids, phages, viruses, and retroviruses. The term "expression cassette" includes a nucleic acid construct containing a gene and having elements in addition to the gene that allow for proper and or enhanced expression of that gene in a host cell. For producing antibodies, nucleic acids encoding light and heavy chains can be inserted into expression vectors. Such sequences can be present in the same nucleic acid molecule (e.g., the same expression vector) or alternatively, can be expressed from separate nucleic acid molecules (e.g., separate expression vectors).

The term "operably linked" includes a juxtaposition wherein the components are in a relationship permitting them to function in their intended manner (e.g., functionally linked). As an example, a promoter/enhancer operably linked to a polynucleotide of interest is ligated to said polynucleotide such that expression of the polynucleotide of interest is achieved under conditions which activate expression directed by the promoter/enhancer.

Expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al., U.S. Pat. No. 4,704,362). In addition to the immunoglobulin DNA cassette sequences, insert sequences, and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin, or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

Once the vector has been incorporated into the appropriate host cell, the host cell is maintained under conditions suitable for high level expression of the nucleotide sequences, and the collection and purification of the desired antibodies. Any host cell susceptible to cell culture, and to expression of proteins or polypeptides, may be utilized in accordance with the present invention. In certain embodiments, the host cell is mammalian. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59, 1977); baby hamster kidney cells (BHK, ATCC CCL 10); Chinese hamster ovary cells +/−DHFR (CHO, Urlaub and Chasin, *Proc. Natl. Acad. Sci.* USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44-68, 1982); MRC 5 cells; FS4 cells; and a human hepatoma line (Hep G2).

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. (See, e.g., Co et al., (1992) *J. Immunol.* 148:1149). Preferred regulatory sequences for mammalian host cell expression include viral elements that direct high levels of protein expression in mammalian cells, such as promoters and/or enhancers derived from FF-1a promoter and BGH poly A, cytomegalovirus (CMV) (such as the CMV promoter/enhancer), Simian Virus 40 (SV40) (such as the SV40 promoter/enhancer), adenovirus (e.g., the adenovirus major late promoter (AdMLP)), and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al. In exemplary embodiments, the antibody heavy and light chain genes are operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. In exemplary embodiments of the invention, the construct include an internal ribosome entry site (IRES) to provide relatively high levels of polypeptides of the invention in eukaryotic host cells. Compatible IRES sequences are disclosed in U.S. Pat. No. 6,193,980 that is also incorporated herein.

Alternatively, coding sequences can be incorporated in a transgene for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Prokaryotic host cells may also be suitable for producing the antibodies of the invention. *E. coli* is one prokaryotic host particularly useful for cloning the polynucleotides (e.g., DNA sequences) of the present invention. Other microbial hosts suitable for use include bacilli, such as *Bacillus subtilis*, enterobacteriaceae, such as *Escherichia, Salmonella*, and *Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Expression of proteins in prokaryotes is most often carried out in *E. coli* with vectors containing constitutive or inducible promoters directing the expression of either fusion or non-fusion proteins. Fusion vectors add a number of amino acids to an antibody encoded therein, often to the constant region of the recombinant antibody, without affecting specificity or antigen recognition of the antibody. Addition of the amino acids of the fusion peptide can add additional function to the antibody, for example as a marker (e.g., epitope tag such as myc or flag).

Other microbes, such as yeast, are also useful for expression. *Saccharomyces* is a preferred yeast host, with suitable vectors having expression control sequences (e.g., promoters), an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally, Sambrook et al., *Molecular Cloning: A Laboratory Manual* (Cold Spring Harbor Press, 2nd ed., 1989), incorporated by reference herein in its entirety for all purposes.). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be separated as described herein and/or further purified according to procedures known in the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

Protein Purification

It is desirable to isolate and/or purify proteins expressed according to the present invention. In certain embodiments, an expressed protein is secreted into the medium and thus cells and other solids may be removed, as by centrifugation or filtering for example, as a first step in the purification process.

In some embodiments, an expressed protein is bound to the surface of the host cell. In such embodiments, the media is removed and the host cells expressing the polypeptide or protein are lysed as a first step in the purification process. Lysis of mammalian host cells can be achieved by any number of means known to those of ordinary skill in the art, including physical disruption by glass beads and exposure to high pH conditions.

A protein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, *Protein Purification Principles and Practice 2nd Edition*, Springer-Verlag, New York, 1987; Higgins, S. J. and Hames, B. D. (eds.), *Protein Expression: A Practical Approach*, Oxford Univ Press, 1999; and Deutscher, M. P., Simon, M. I., Abelson, J. No. (eds.), *Guide to Protein Purification: Methods in Enzymology* (Methods in Enzymology Series, Vol 182), Academic Press, 1997, each of which is incorporated herein by reference in its entirety). For immunoaffinity chromatography in particular, the protein may be isolated by binding it to an affinity column comprising antibodies that were raised against that protein and were affixed to a stationary support. Affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly advantageous when cells must be lysed in order to isolate and purify the expressed polypeptide or protein.

Proteins expressed according to certain methods of the present invention may have more extensive and/or modified glycosylation patterns than they would if grown under non-inventive cell culture conditions. Thus, one practical benefit of the present invention that may be exploited at the purification step is that the additional and/or modified sugar residues present on a glycoprotein grown in accordance with certain of the present inventive methods and/or compositions may confer on it distinct biochemical properties that may be used by the practitioner to purify that glycoprotein more easily, or to a greater purity, than would be possible for a glycoprotein grown in accordance with non-inventive methods and/or compositions.

One of ordinary skill in the art will appreciate that the exact purification technique may vary depending on the character of the polypeptide or protein to be purified, the character of the cells from which the polypeptide or protein is expressed, and/or the composition of the medium in which the cells were grown.

Pharmaceutical Formulations

The protein preparations of the invention can be formulated as pharmaceutical compositions in the presence of a pharmaceutically acceptable carrier or excipient. Compositions containing the protein preparations, as described herein, may be administered to a subject or may first be formulated for delivery by any available route including, but not limited to parenteral, intravenous, intramuscular, intradermal, subcutaneous, oral, buccal, sublingual, nasal, bronchial, opthalmic, transdermal (topical), transmucosal, rectal, and vaginal routes. Inventive pharmaceutical compositions typically include a purified polypeptide or protein expressed from a mammalian cell line, a delivery agent (i.e., a cationic polymer, peptide molecular transporter, surfactant, etc., as described above) in combination with a pharmaceutically acceptable carrier. As used herein, the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into compositions of the present invention. For example, a protein or polypeptide produced according to the present invention may be conjugated to drugs for systemic pharmacotherapy, such as toxins, low-molecular-weight cytotoxic drugs, biological response modifiers, and radionuclides (see e.g., Kunz et al., Calicheamicin derivative-carrier conjugates, U.S. Ser No. 04/0082764 A1). Additional ingredients useful in preparing pharmaceutical compositions in accordance with the present invention include, for example, flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof.

Alternatively or additionally, a protein or polypeptide produced according to the present invention may be administered in combination with (whether simultaneously or sequentially) one or more additional pharmaceutically active agents. An exemplary list of these pharmaceutically active agents can be found in the *Physicians' Desk Reference,* 55 Edition, published by Medical Economics Co., Inc., Montvale, N.J., 2001, incorporated herein by reference. For many of these listed agents, pharmaceutically effective dosages and regimens are known in the art; many are presented in the Physicians' Desk Reference itself.

Solid pharmaceutical compositions may contain one or more solid carriers, and optionally one or more other additives such as flavoring agents, lubricants, solubilizers, suspending agents, fillers, glidants, compression aids, binders or tablet-disintegrating agents or an encapsulating material. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier may be a finely divided solid which is in admixture with the finely divided active ingredient. In tablets, the active ingredient is generally mixed with a carrier having the necessary compression properties in suitable proportions, and optionally, other additives, and compacted into the desired shape and size.

Liquid pharmaceutical compositions may contain the polypeptide or protein expressed according to the present invention and one or more liquid carriers to form solutions, suspensions, emulsions, syrups, elixirs, or pressurized compositions. Pharmaceutically acceptable liquid carriers include, for example water, organic solvents, pharmaceutically acceptable oils or fat, or combinations thereof. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators, or combinations thereof. If the liquid formulation is intended for pediatric use, it is generally desirable to avoid inclusion of, or limit the amount of, alcohol.

Examples of liquid carriers suitable for oral or parenteral administration include water (optionally containing additives such as cellulose derivatives such as sodium carboxymethyl cellulose), alcohols or their derivatives (including monohydric alcohols or polyhydric alcohols such as glycols) or oils (e.g., fractionated coconut oil and arachis oil). For parenteral administration the carrier can also be an oily ester such as ethyl oleate and isopropyl myristate. The liquid carrier for pressurized compositions can be halogenated hydrocarbons or other pharmaceutically acceptable propellant.

Liquid pharmaceutical compositions which are sterile solutions or suspensions can be administered parenterally, for example by, intramuscular, intraperitoneal, epidural, intrathecal, intravenous or subcutaneous injection. Pharmaceutical compositions for oral or transmucosal administration may be either in liquid or solid composition form.

In certain embodiments, a pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition should be sterile and should be fluid to the extent that easy syringability exists. Advantageously, certain pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In certain cases, it will be useful to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the purified polypeptide or protein in the required amount in an appropriate solvent with one or a combination of ingredients enumerated above, as required, followed by filtered sterilization. Generally, dispersions are prepared by incorporating the purified polypeptide or protein expressed from a mammalian cell line into a sterile vehicle which contains a basic dispersion medium and the required other ingredients from those enumerated above. In the case of sterile powders for the preparation of sterile injectable solutions, advantageous methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the purified polypeptide or protein can be incorporated with excipients and used in the form of tablets, troches, or capsules, e.g., gelatin capsules. Oral compositions can also be prepared using a fluid carrier, e.g., for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Such preparations may be mixed chewable or liquid formulations or food materials or liquids if desirable, for example to facilitate administration to children, to individuals whose ability to swallow tablets is compromised, or to animals. Formulations for oral delivery may advantageously incorporate agents to improve stability within the gastrointestinal tract and/or to enhance absorption.

For administration by inhalation, inventive compositions comprising a protein preparation expressed from a mammalian cell line and a delivery agent can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered, for example a therapeutically effective amount. The present invention particularly contemplates delivery of inventive compositions using a nasal spray, inhaler, or other direct delivery to the upper and/or lower airway. Intranasal administration of DNA vaccines directed against influenza viruses has been shown to induce CD8 T cell responses, indicating that at least some cells in the respiratory tract can take up DNA when delivered by this route, and inventive delivery agents will enhance cellular uptake. According to certain embodiments, compositions comprising a purified polypeptide expressed from a mammalian cell line and a delivery agent are formulated as large porous particles for aerosol administration.

Modified release and pulsatile release oral dosage forms may contain excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release oral dosage forms may contain one or a combination of release rate modifying excipients. Release rate modifying excipients may be present both within the dosage form i.e., within the matrix, and/or on the dosage form, i.e., upon the surface or coating.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified polypeptide or protein and delivery agents can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Alternatively, the compounds can be administered in the form of a suppository or pessary, or they may be applied topically in the form of a gel, hydrogel, lotion or other glycerides, solution, cream, ointment or dusting powder.

In some embodiments, compositions are prepared with carriers that will protect the protein against rapid elimination from the body, such as a controlled release formulation, including implants and microencapsulated delivery systems.

In general, inventive compositions may be formulated for immediate, delayed, modified, sustained, pulsed, or controlled-release delivery. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Suitable materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Proteins produced according to the present invention may also be used in combination with a cyclodextrin. Cyclodextrins are known to form inclusion and non-inclusion complexes with certain molecules. Formation of a cyclodextrin complex may modify the solubility, dissolution rate, bioavailability and/or stability property of a protein or polypeptide. Cyclodextrin complexes are generally useful for most dosage forms and administration routes. As an alternative to direct complexation with the protein or polypeptide, the cyclodextrin may be used as an auxiliary additive, e.g. as a carrier, diluent or solubiliser. Alpha-, beta- and gamma-cyclodextrins are most commonly used and suitable examples are described in published international patent applications WO91/11172, WO94/02518 and WO98/55148.

In some embodiments, pharmaceutical compositions of the present invention are provided in unit dosage form, such as tablets or capsules. It may be advantageous to formulate oral or parenteral compositions in unit dosage form for ease of administration and uniformity of dosage. In such form, the composition is sub-divided in unit dose containing appropriate quantities of the polypeptide or protein. The unit dosage forms can be packaged compositions, for example packeted powders, vials, ampoules, pre-filled syringes or sachets containing liquids. The unit dosage form can be, for example, a capsule or tablet itself, or it can be an appropriate number of any such compositions in package form. As one skilled in the art will recognize, therapeutically effective unit dosage will depend on several factors, including, for example, the method of administration, the potency of the polypeptide or protein, and/or the weight of the recipient and the identities of other components in the pharmaceutical composition.

A protein preparation, e.g., pharmaceutical composition containing the same, can be administered at various intervals and over different periods of time as required, e.g., one time per week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a polypeptide or protein as described herein may comprise a single treatment or a series of treatments. It is furthermore understood that appropriate doses may depend upon the potency of the polypeptide or protein and may optionally be tailored to the particular recipient, for example, through administration of increasing doses until a preselected desired response is achieved. It is understood that the specific dose level for any particular animal subject may depend upon a variety of factors including the activity of the specific polypeptide or protein employed, the age, body weight, general health, gender, and diet of the subject, the time of administration, the route of administration, the rate of excretion, any drug combination, and the degree of expression or activity to be modulated.

The present invention encompasses the use of the compositions described herein for treatment of nonhuman animals. Accordingly, doses and methods of administration may be selected in accordance with known principles of veterinary pharmacology and medicine. Guidance may be found, for example, in Adams, R. (ed.), *Veterinary Pharmacology and Therapeutics*, 8th edition, Iowa State University Press; ISBN: 0813817439; 2001.

The pharmaceutical compositions can be included in a container, pack, or dispenser together with instructions for administration.

The following examples are illustrative and not intended to be limiting.

EXAMPLES

Solutions of the Antibodies M1-M3 were evaluated by static light scattering, dynamic light scattering and asymmetric flow field flow fractionation at different salt concentrations, i.e., different ionic strength.

Antibody Solution Preparation

All solutions were prepared by dialysis into appropriate salt-containing buffer solution at room temperature, overnight with two buffer exchanges.

Instrumental Methods:

Static Light Scattering

Static light scattering (SEC-MALS) was used to measure the weight average molecular weights of the antibody solutions. For the static light scattering experiments, the antibody solutions were diluted to 4 mg/mL and multiple samples were manually injected into the instrument. The antibody solutions were measured at 20° C. using static light scattering at multiple angles (45, 90 and 135) using a Mini Dawn instrument from Wyatt Technology. The scatter data at 90° was used to calculate the weight average molecular weight. The complete data sets (multiple angles) were used to create Zimm plots that were used to calculate molecular weight and second virial coefficients.

Dynamic Light Scattering

Dynamic light scattering was used to measure the particle size of the antibodies in solution. The antibody solutions were measured at 90° angle at 25° C. using a DynaPro instrument from Wyatt Technology.

Asymmetric Flow Field Flow Fractionation

Asymmetric Flow Field Flow Fractionation (AF4) was also used to measure the particle size of the antibodies in solutions. AF4 measurements were performed on an Eclipse instrument from Wyatt Technology. AF4 analysis parameters were as follows: temperature 20 C, running buffer is the same as the dialysis buffer, 10 KDa cutoff membrane.

Optical Density

Turbidity of a protein sample was measured as an apparent optical density (absorbance of light at a specific wavelength) using a SpectraMax UV-Vis at a wavelength of 400 nm.

Example 1

Analysis of IgG1 Antibody M1 (Myo-029)

Figure 1:
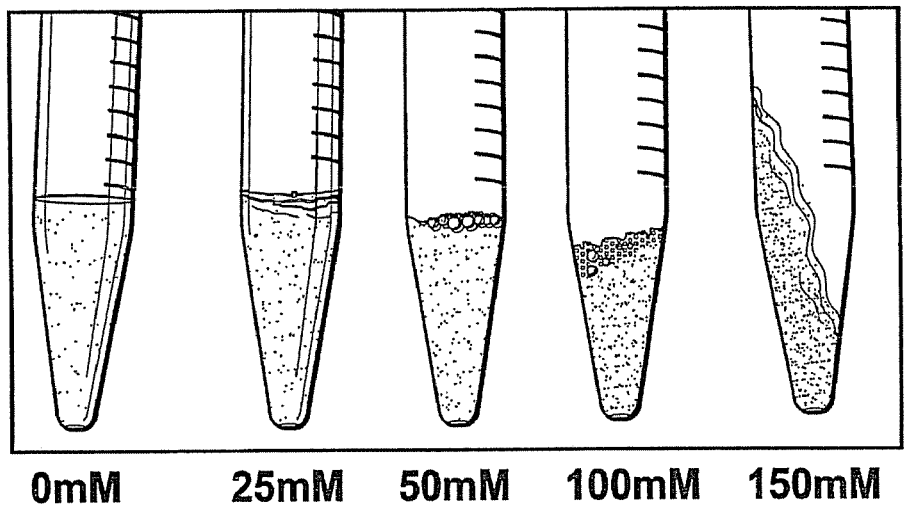
FIG. 1 shows images of Antibody M1 (also referred to herein as "Myo-029") solutions exposed to increasing NaCl concentration (showing a visually perceptible opalescence increase).
Figure 2:
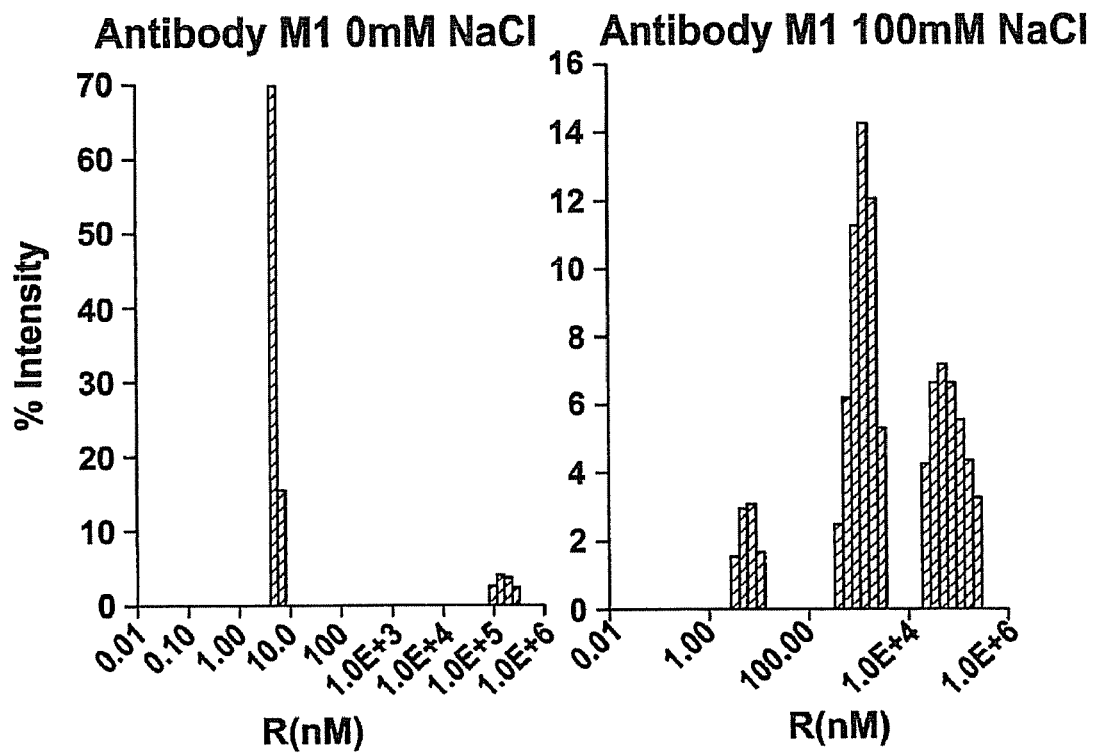
FIG. 2 shows dynamic light scattering plots for Antibody M1 solutions in 0 mM NaCl and 100 mM NaCl.

Antibody M1 solutions exhibit a large opalescence effect depending on salt concentration, i.e., ionic strength. FIG. 1 shows the visually perceptible change in opalescence as concentrations increase from 0 mM NaCl to 150 mM NaCl at approximately 20 mg/mL of protein. Antibody M1 solutions ranging from 0 mM NaCl to 100 mM NaCl were also analyzed by dynamic light scattering, samples were diluted to approximately 5 mg/mL. The data collected are shown in Table 1. FIG. 1 shows images of Antibody M1 (also referred to herein as "Myo-029") solutions exposed to increasing NaCl concentration (showing a visually perceptible opalescence increase). FIG. 2 shows the dynamic light scattering plots for the 0 mM NaCl solution and the 100 mM NaCl Antibody M1 solutions the data for which is included in Table 1.

TABLE 1

Dynamic Light Scattering Data for Antibody M1

|  | "Peak 1" | | "Peak 2" | | "Peak 3" | |
| --- | --- | --- | --- | --- | --- | --- |
|  | MW (kDa) | % Mass | MW (kDa) | % Mass | MW (kDa) | % Mass |
| 0 mM NaCl | 139 | 98.0 | — | — | $5.49 \times 10^{12}$ | 2.0 |
| 25 mM NaCl (top layer)[a] | 266 | 96.6 | — | — | $2.19 \times 10^{11}$ | 3.4 |
| 25 mM NaCl (bottom layer) | 268 | 96.8 | — | — | $1.03 \times 10^{12}$ | 3.2 |
| 50 mM NaCl (top layer) | 290 | 88.8 | — | — | $2.59 \times 10^{11}$ | 11.2 |
| 50 mM NaCl (bottom layer) | 342 | 85.8 | — | — | $5.27 \times 10^{12}$ | 14.2 |
| 100 mM NaCl | 353 | 64.4 | $9.04 \times 10^{7}$ | 0.8 | $1.18 \times 10^{12}$ | 34.8 |

[a]The 25 mM and 50 mM solutions exhibited a phase separation with top and bottom layers. Both layers contained antibodies.

The increase in % mass of the Peak 2 and Peak 3 species correlates with the increase in opalescence that is visually perceptible in FIG. 1. The presence of Peak 3 in the 0 mM NaCl solution indicates that a small amount of the opalescent species is present even at low salt concentrations for Antibody M1.

Figure 3:
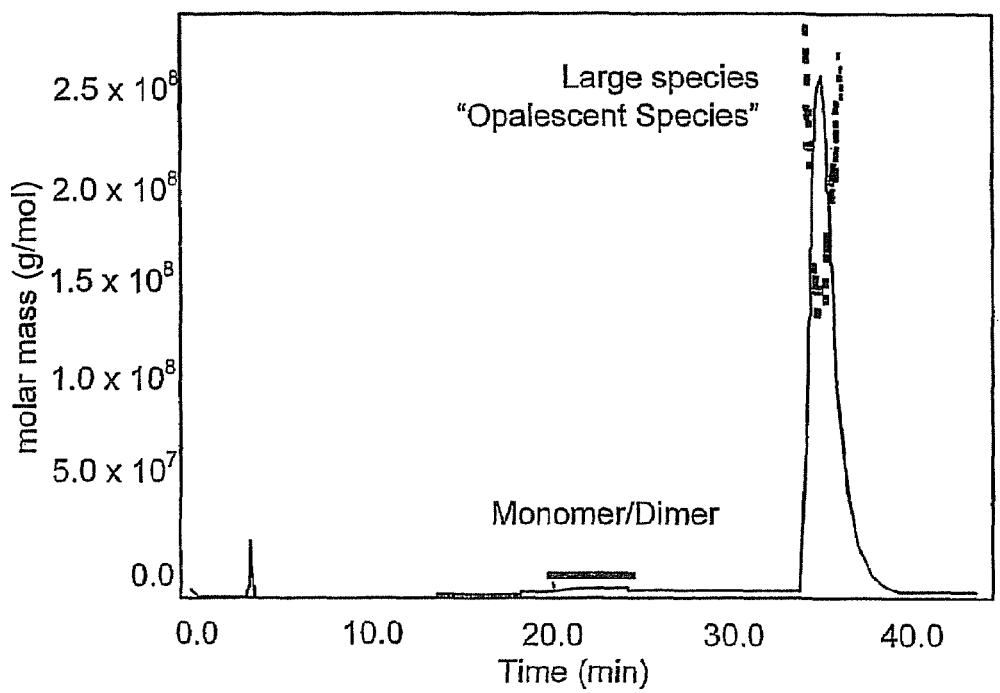
FIG. 3 shows an asymmetric flow field flow fractionation plot for an Antibody M1 solution in 100 mM NaCl.
Figure 4:
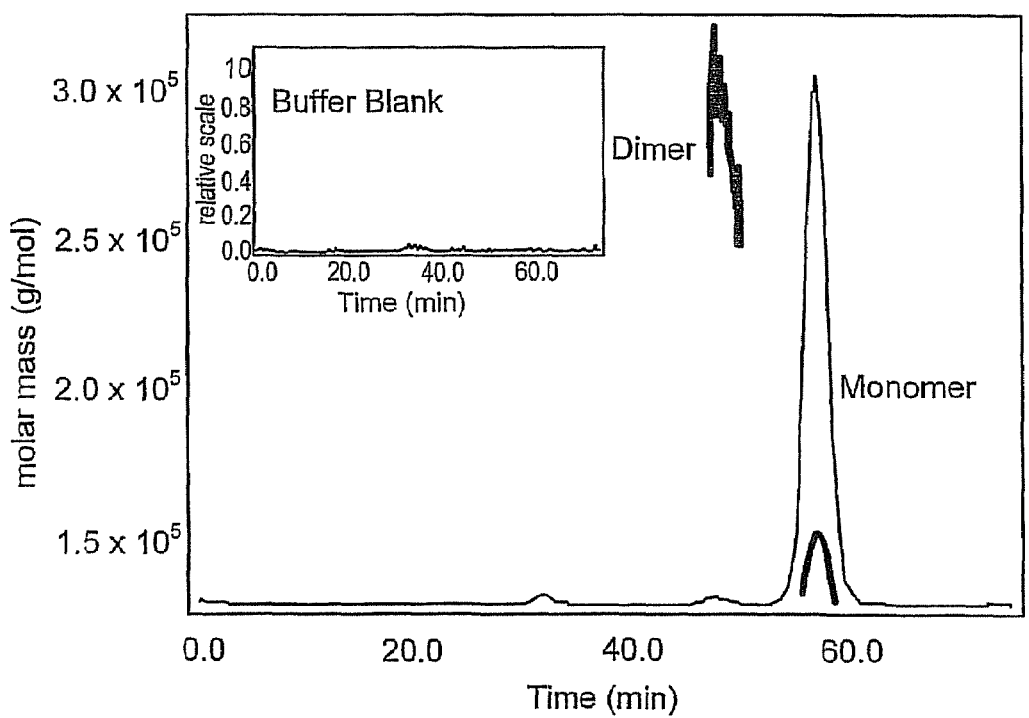
FIG. 4 shows a SEC-HPLC chromatograph for an Antibody M1 solution in 100 mM NaCl.

Asymmetric flow field flow fractionation of a 100 mM NaCl solution of Antibody M1 (at 20 mg/mL protein) indicated a large species as shown in FIG. 3. SEC-HPLC (samples diluted to 3 mg/mL) was unable to discern any large species for a similar 100 mM NaCl solution of Antibody M1 as shown in FIG. 4.

Figure 5:
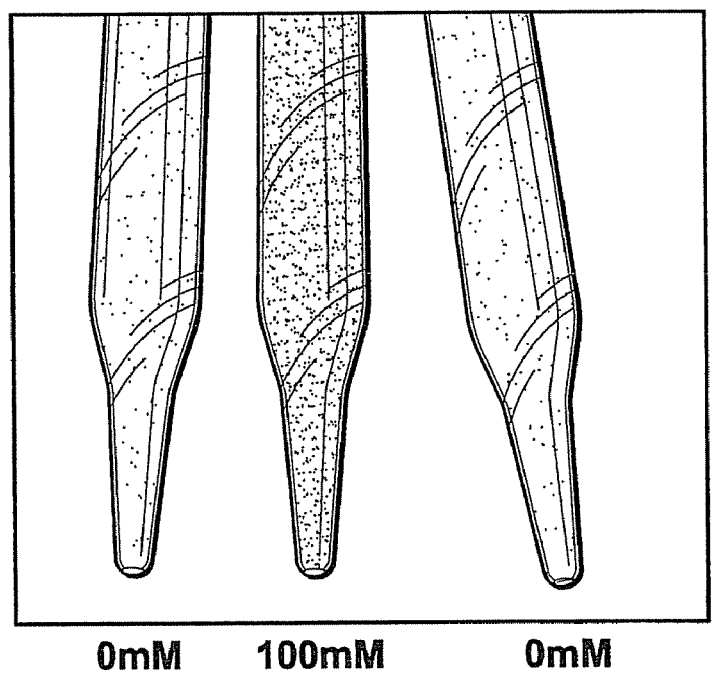
FIG. 5 shows images of Antibody M1 solutions that have been dialyzed from 0 mM NaCl to 100 mM NaCl and back to 0 mM NaCl (showing visibly reversible opalescence with changes in salt concentration).
Figure 6:
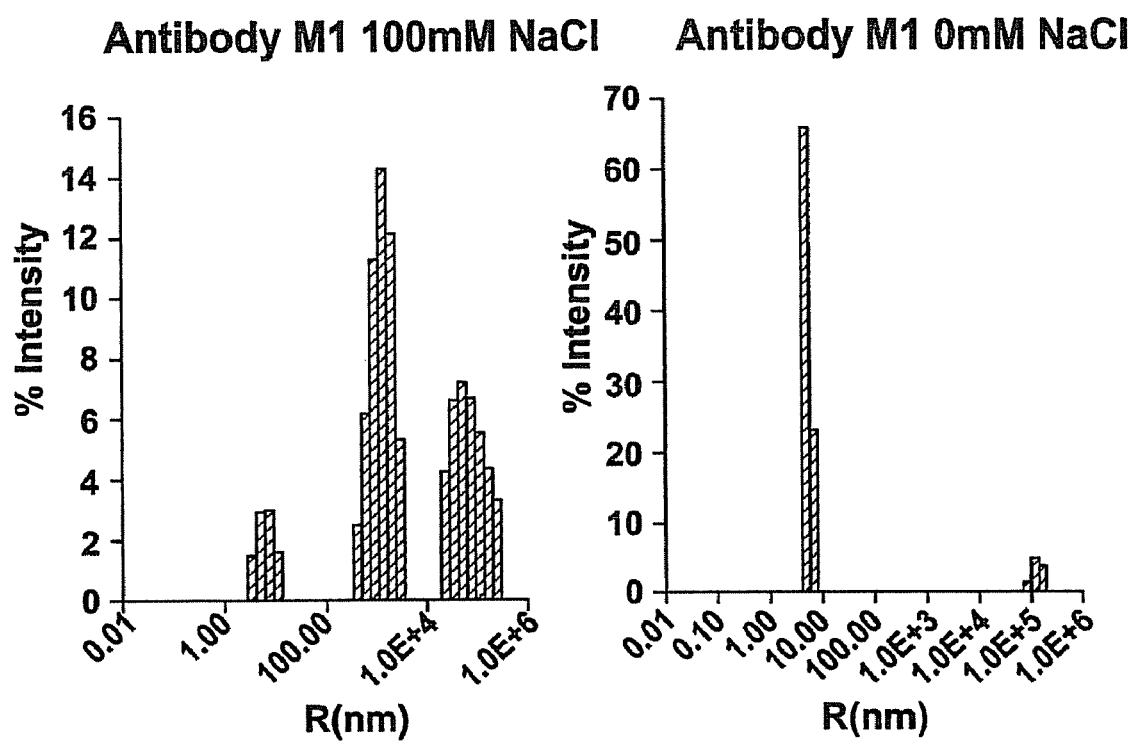
FIG. 6 shows dynamic light scattering plots of Antibody M1 solutions showing reversible formation of opalescent species: (a) 100 mM NaCl, which was dialyzed from 0 mM NaCl, and (b) 0 mM NaCl, which was dialyzed from 100 mM NaCl.

The reversibility of the opalescence effect for Antibody M1 was also examined. An Antibody M1 solution was dialyzed from 0 mM NaCl to 100 mM NaCl and then back to 0 mM NaCl. Antibody M1 was dialyzed overnight into a 100 mM NaCl solution (originally in a salt free solution), then a small amount of this material at 100 mM NaCl was dialyzed overnight back into a salt-free solution. FIG. 5 shows the visually perceptible change in opalescence for these three Antibody M1 solutions. FIG. 6 shows dynamic light scattering plots for the opalescent 100 mM NaCl intermediate dialysis solution and also the 0 mM NaCl final dialysis solution.

These data indicate that Antibody M1 contains an extremely large species, though the species is only present in a relatively small amount at 0 mM NaCl, and that the concentration of this large species increases with increasing salt concentration. The data also show that the large species can be discerned using asymmetric flow field flow fractionation, but is too large to make it onto an SEC-HPLC column, is disrupted by the bedding, or is disrupted upon dilution. Fortunately, the large species can be resolved and analyzed using dynamic light scattering as shown.

Example 2

Analysis of IgG 1 Antibody M2

Figure 7:
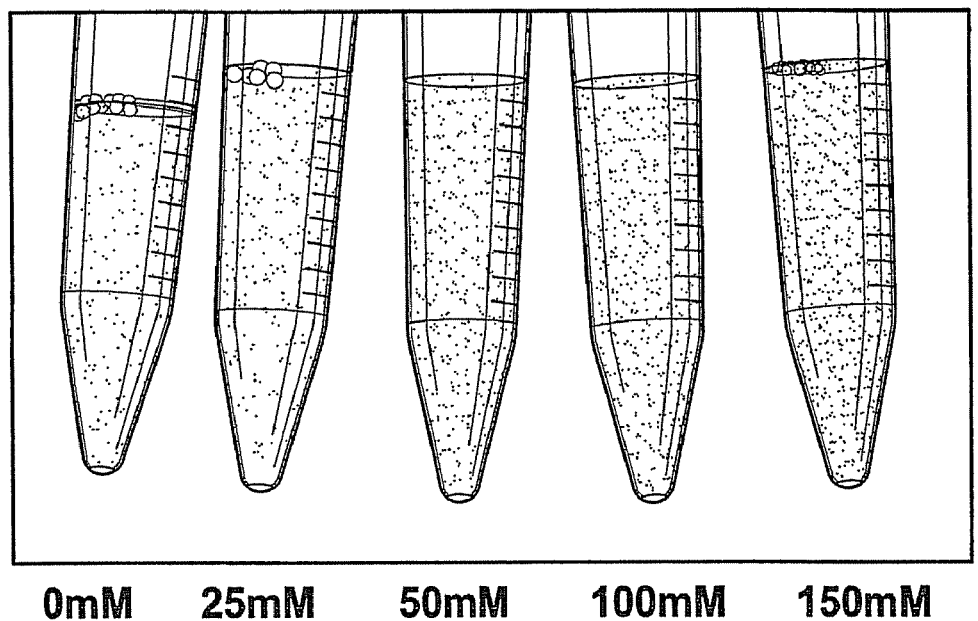
FIG. 7 shows images of Antibody M2 solutions with increasing NaCl concentration (showing no visually perceptible opalescence increase).
Figure 8:
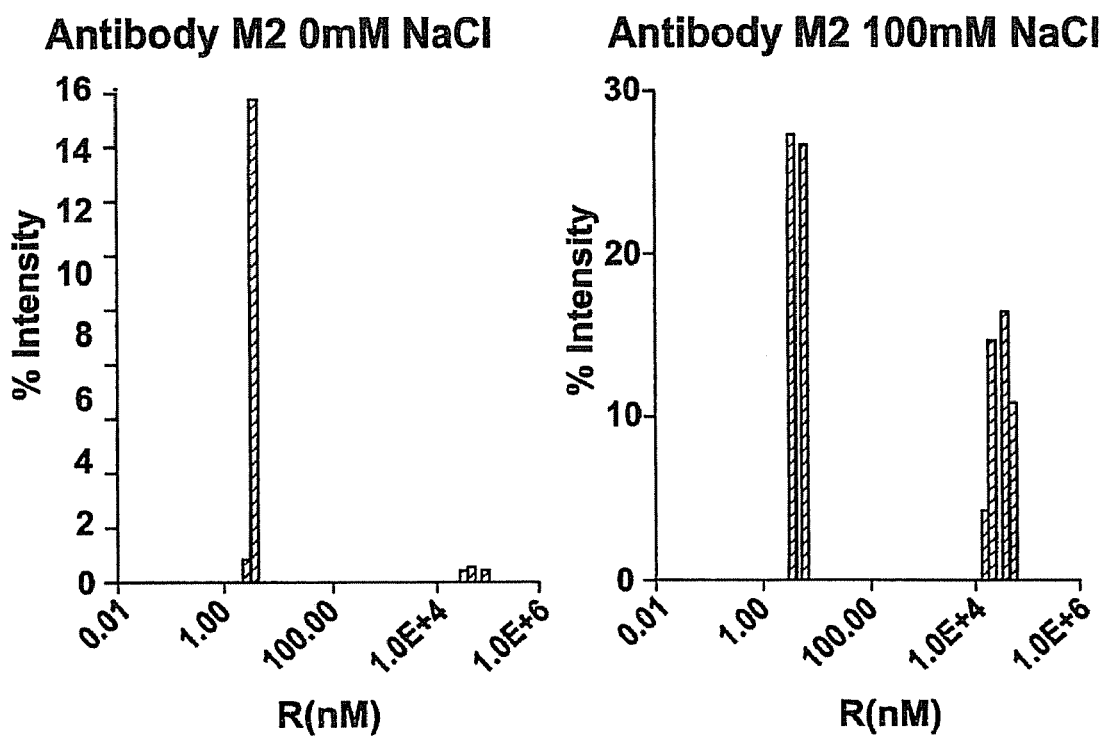
FIG. 8 shows dynamic light scattering plots for Antibody M2 solutions in 0 mM NaCl and 150 mM NaCl.

Antibody M2 solutions do not exhibit a large opalescence effect over the concentration ranges relevant to subcutaneous antibody dosing. FIG. 7 shows the lack of a visually perceptible change in opalescence as concentrations increase from 0 mM NaCl to 150 mM NaCl at approximately 20 mg/mL of protein. Antibody M2 solutions of 0 mM NaCl and 150 mM NaCl were also analyzed by dynamic light scattering at approximately 5 mg/mL of protein. The dynamic light scattering data collected are shown in Table 2. FIG. 8 shows the dynamic light scattering plots for the 0 mM NaCl solution and the 150 mM NaCl Antibody M2 solutions the data for which is included in Table 2.

TABLE 2

Dynamic Light Scattering Data for Antibody M2

|  | "Peak 1" | | "Peak 2"[a] | | "Peak 3" | |
| --- | --- | --- | --- | --- | --- | --- |
|  | MW (kDa) | % Mass | MW (kDa) | % Mass | MW (kDa) | % Mass |
| 0 mM NaCl | 130 | 99.8 | — | — | $3.89 \times 10^{11}$ | 0.2 |
| 150 mM NaCl | 129 | 98.0 | — | — | $1.23 \times 10^{11}$ | 2.0 |

[a]"Peak 2" is only included for purposes of comparison to Table 1.

These data show that Antibody M2 does not have an appreciable amount of an opalescent species in the concentration range relevant to subcutaneous dosing. In fact, the Peak 3 percent mass only rises at the 150 mM NaCl level to the percent mass level for Antibody M at 0 mM NaCl.

Example 3

Analysis of Antibody M3

Antibody M3 solutions do not exhibit a large opalescence effect over the concentration ranges evaluated. Antibody M3 solutions of 0 mM NaCl and 150 mM NaCl were analyzed by dynamic light scattering at approximately 5 mg/mL. The dynamic light scattering data collected are shown in Table 3.

Figure 9:
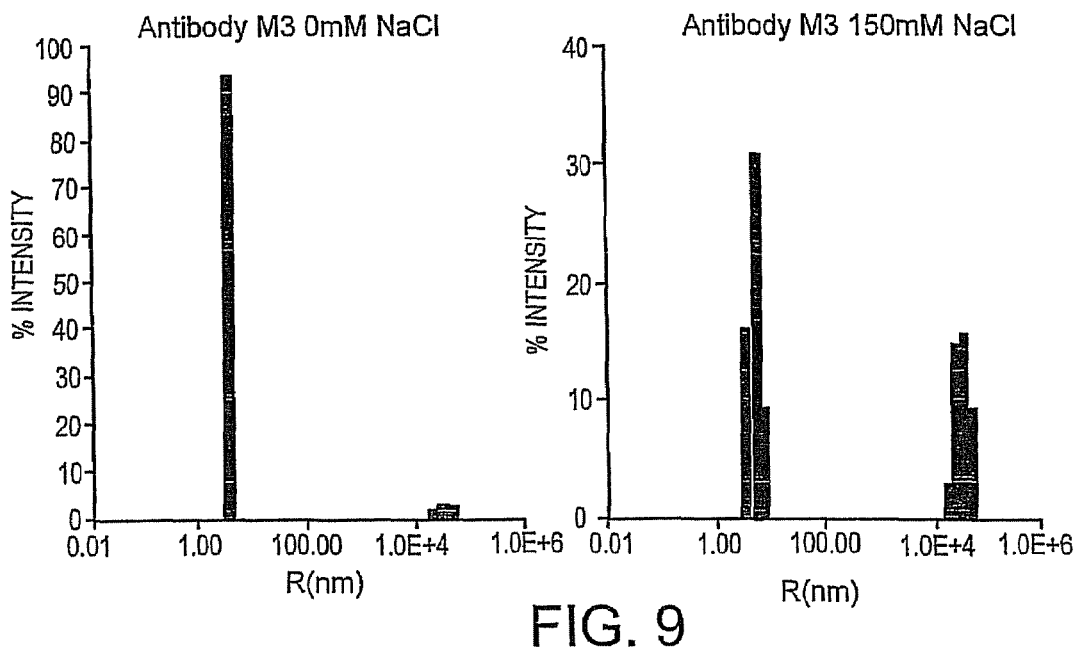
FIG. 9 shows dynamic light scattering plots for Antibody M3 solutions in 0 mM NaCl and 150 mM NaCl.

FIG. 9 shows the dynamic light scattering plots for the 0 mM NaCl solution and the 150 mM NaCl Antibody M3 solutions, the data for which are included in Table 3.

TABLE 3

Dynamic Light Scattering Data for Antibody M3

|  | "Peak 1" | | "Peak 2"[a] | | "Peak 3" | |
| --- | --- | --- | --- | --- | --- | --- |
|  | MW (kDa) | % Mass | MW (kDa) | % Mass | MW (kDa) | % Mass |
| 0 mM NaCl | 178 | 99.9 | — | — | $1.68 \times 10^{11}$ | 0.1 |
| 150 mM NaCl | 191 | 97.4 | — | — | $1.22 \times 10^{11}$ | 2.6 |

[a]"Peak 2" is only included for purposes of comparison to Table 1.

These data show that Antibody M3 does not have an appreciable amount of an opalescent species in the concentration range evaluated. In fact, the Peak 3 percent mass only rises at the 150 mM NaCl level to a percent mass level just higher than that for Antibody M1 at 0 mM NaCl.

Example 4

Evaluation of Second Virial Coefficients

Static light scattering was used to determine the molecular weights and second virial coefficients (A2) for the antibodies analyzed in Examples 1-3 (Antibody M1, Antibody M2, and Antibody M3). Second virial coefficient measurements can be determined using static light scattering and Zimm analysis. The experiment is conducted by injecting multiple dilute protein samples manually into a light scattering system. Using these multiple measurements and precise concentrations, a Zimm plot can be constructed. These data are shown in Table 4.

TABLE 4

Molecular Weight and Second Virial Coefficient Data Calculated from Static Light Scattering Data

| Sample | MW (kDa) | A2 [mol-mL/g$^2$] |
|---|---|---|
| Antibody M1 (0 mM NaCl) | 131 | $-3.62x^{-4}$ |
| Antibody M1 (100 mM NaCl) | 130 | $-2.41x^{-3}$ |
| Antibody M2 (0 mM NaCl) | 149 | $3.29x^{-4}$ |
| Antibody M2 (150 mM NaCl) | 148 | $6.77x^{-4}$ |
| Antibody M3 (0 mM NaCl) | 181 | $2.05x^{-3}$ |
| Antibody M3 (150 mM NaCl) | 156 | $1.29x^{-3}$ |

The second virial coefficient data show the aggregation/association tendencies of Antibody M1, i.e., negative second virial coefficients, as compared to Antibody M2 and Antibody M3, which have positive virial coefficients. FIG. 10 shows a second virial coefficient plot for Antibody M1 at 100 mM NaCl and FIG. 11 shows a second virial coefficient plot for Antibody M2 at 150 mM NaCl from a concentration range of 0.1 to 1.1 mg/mL of protein. These data indicate that the second virial coefficient can be used as a predictor of opalescence for a particular antibody.

Example 5

Effects of Salt Identity and Concentration on Opalescence in Antibody M1

To evaluate the effects of salt identity on the opalescence of Antibody M1, several experiments were conducted.

Figure 12:
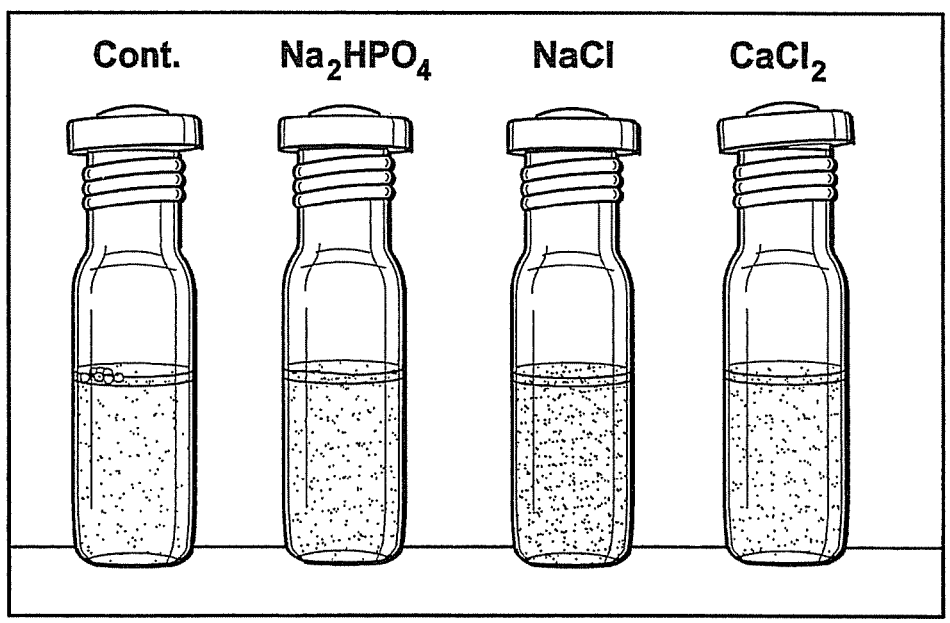
FIG. 12 shows images of Antibody M1 solutions containing different salts showing opalescence after one hour.

Opalescence Change with Salt Identity Over Time:

Four 63 mg/mL Antibody M1 solutions were prepared: a control solution with no salt, a solution with 100 mM Na$_2$HPO$_4$, a solution with 100 mM NaCl, and a solution with 100 mM CaCl$_2$. These solutions were then allowed to sit at room temperature for one hour. Images of these solutions after one hour are shown in FIG. 12. As can be seen in FIG. 12, the order of opalescence after one hour is NaCl>Na$_2$HPO$_4$>CaCl$_2$. This image also shows that opalescence is not solely related to the presence of chloride ions, i.e., the Na$_2$HPO$_4$ solution developed opalescence.

Figure 13:
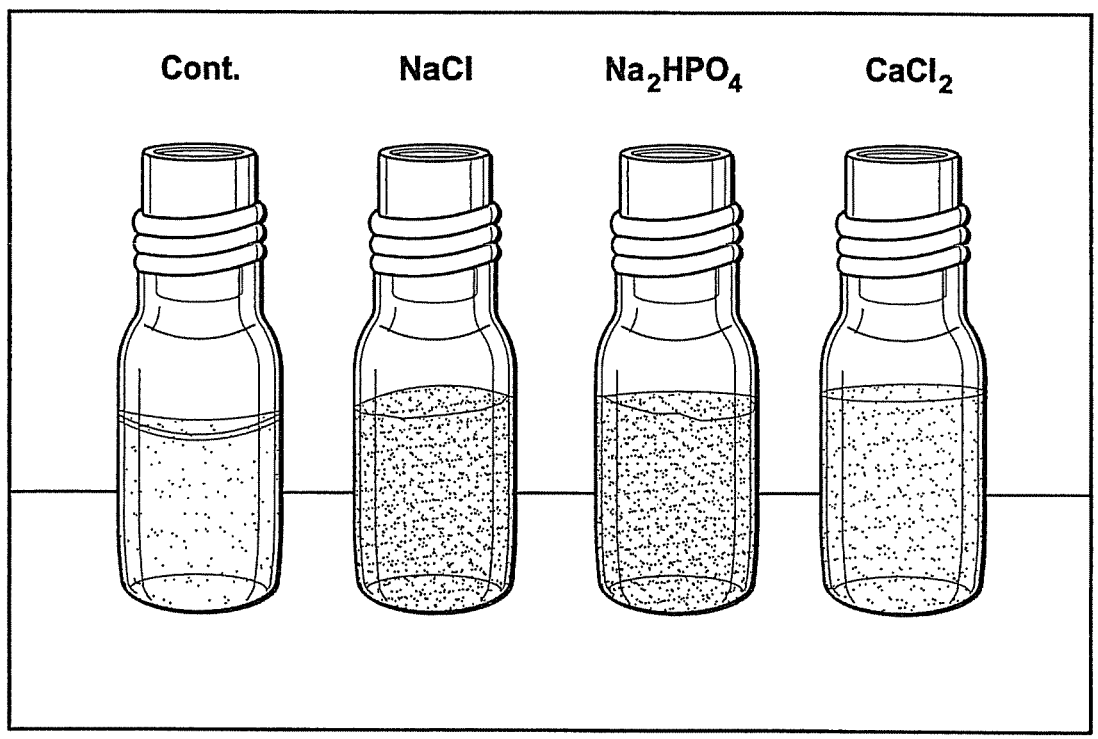
FIG. 13 shows images of Antibody M1 solutions containing different salts showing opalescence after two weeks.

These same solutions were then kept at 2-8° C. for two weeks. Images of these solutions after two weeks are shown in FIG. 13. Each of these solutions shown in FIG. 13 showed gelling after two weeks at 2-8° C. and developed opalescence. However, the degree of gelling and opalescence was salt type and concentration dependent. The order of opalescence was the same as after one hour: NaCl>Na$_2$HPO$_4$>CaCl$_2$. Also tested, but not shown at this time, was the salt MgCl$_2$, which fit into the scheme as follows: NaCl>Na$_2$HPO$_4$>MgCl$_2$>CaCl$_2$.

Figure 14:
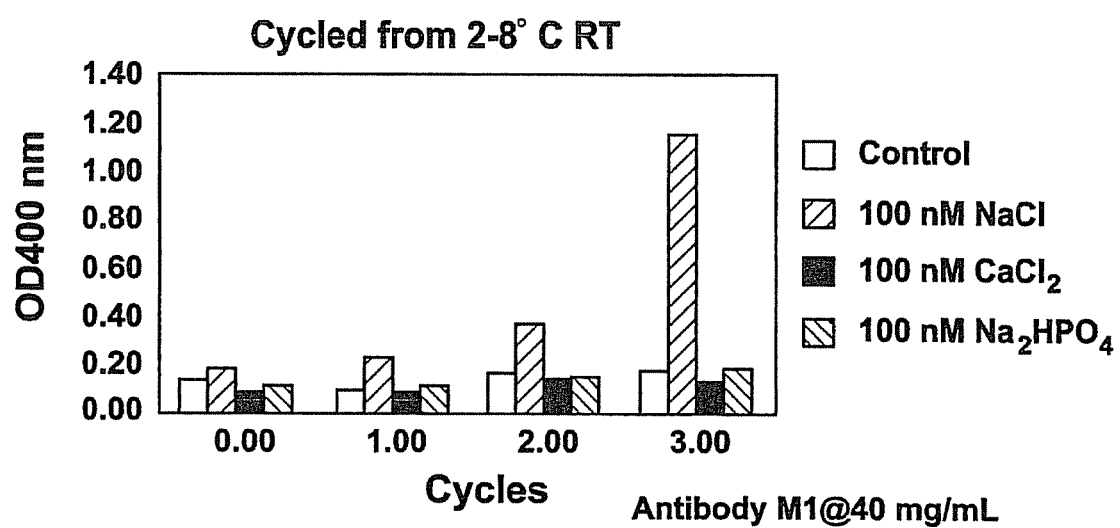
FIG. 14 shows a plot of OD400 nm versus number of temperatures cycles for Antibody M1 solutions containing different salts.

Opalescence Change with Salt Identity and Temperature Cycling:

Changes in optical density at 400 nm was used to monitor the effect of salt identity on opalescence during temperature cycling. For this experiment, four 40 mg/mL Antibody M1 solutions were prepared: a control solution with no salt, a solution with 100 mM Na$_2$HPO$_4$, a solution with 100 mM NaCl, and a solution with 100 mM CaCl$_2$. These solutions were cycled from 2-8° C. to room temperature for three cycles. Each cycle from 2-8° C. to room temperature and back to 2-8° C. took 24 hours. A plot of OD400 nm versus number of cycles is shown in FIG. 14. The increasing OD400 nm values for the NaCl solution, for example, indicates the increasing formation of secondary structure. Thus, the data in FIG. 14 shows that cycling between liquid and gel likely increases opalescence.

Figure 15:
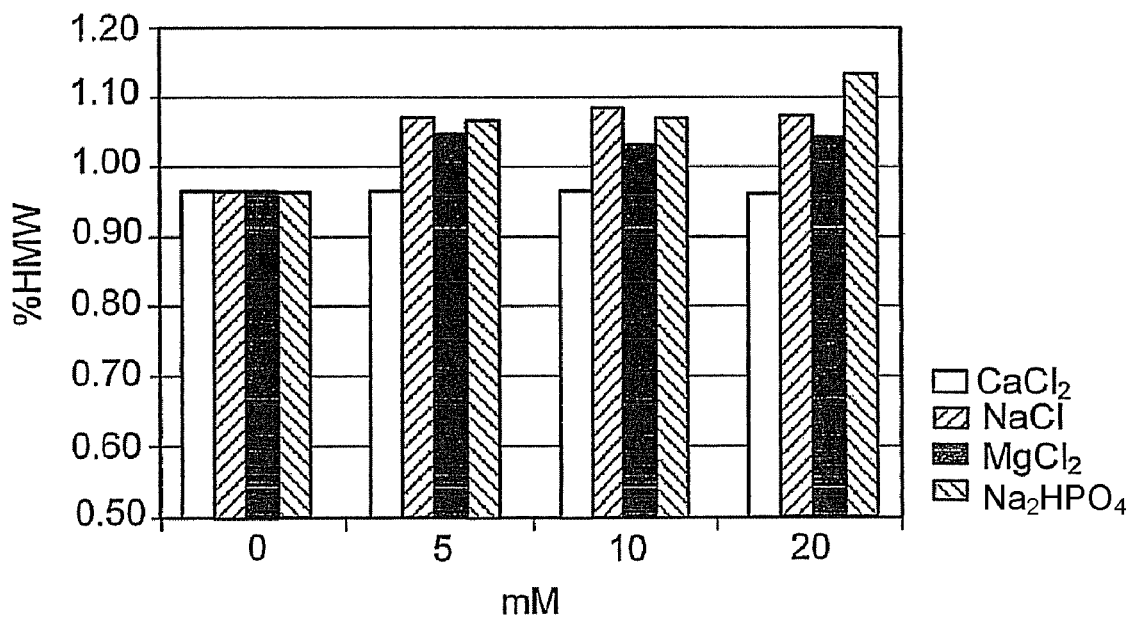
FIG. 15 shows a plot of percent high molecular weight versus salt concentration for Antibody M1 solutions containing different salts.

Opalescence Change with Salt Identity and Concentration:

Percent high molecular weight changes were monitored by SEC-HPLC for changes in salt concentration. For this experiment, CaCl$_2$, NaCl, MgCl$_2$, and Na$_2$HPO$_4$ solutions were prepared at 0, 5, 10, and 20 mM concentrations. The percent high molecular weight material was measured for each sample. A plot of percent high molecular weight versus concentration is shown in FIG. 15. The percent high molecular weight species increase for each salt except CaCl$_2$.

Figure 16:
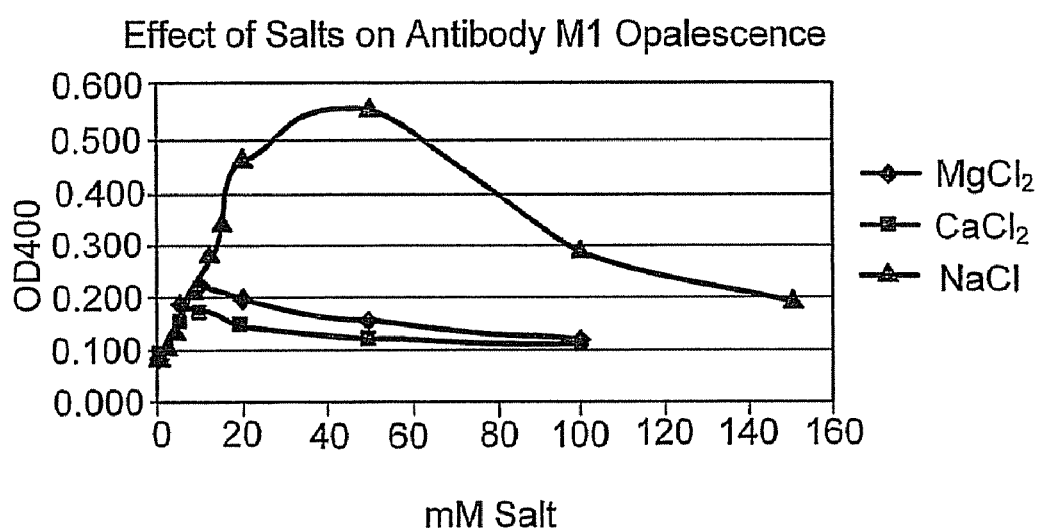
FIG. 16 shows a plot of OD400 nm versus salt concentration for Antibody M1 solutions containing different salts.
Figure 17:
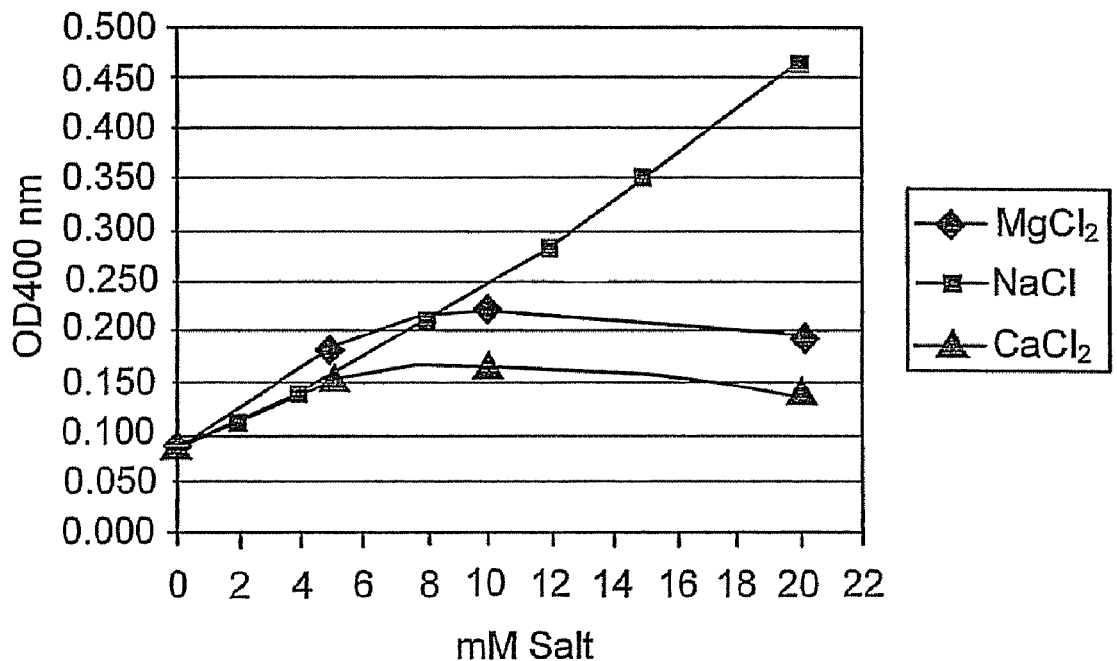
FIG. 17 shows an expanded region of the plot shown in FIG. 16.

Changes in Optical Density with Salt Identity and Concentration:

Changes in optical density at 400 nm were used to monitor the effect of salt identity and concentration on opalescence. For this experiment, a series of Antibody M1 solutions were prepared using MgCl$_2$, CaCl$_2$ and NaCl salts. A plot of OD400 nm versus salt concentration is shown in FIG. 16. FIG. 17 shows an expanded region of the data in FIG. 16. These data illustrate that high molecular weight species increases at increasing concentration of NaCl and only slightly increases for CaCl$_2$ and MgCl$_2$.

Figure 18:
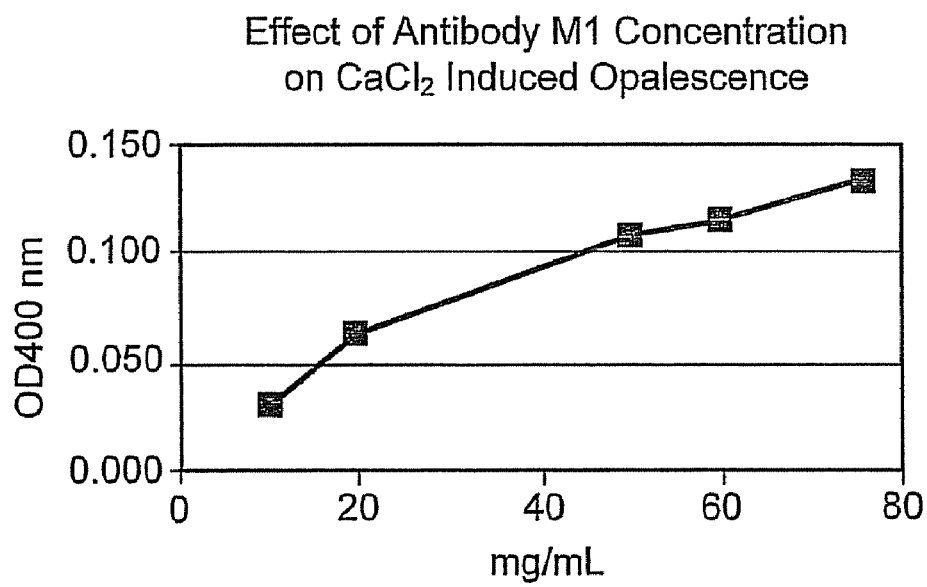
FIG. 18 shows a plot of OD400 nm versus Antibody M1 concentration in 20 mM $CaCl_2$.

Changes in Optical Density with Respect to Antibody M1 Concentration in 20 mM CaCl$_2$:

Finally, changes in optical density at 400 nm were used to monitor the effect of changing Antibody M1 concentration in a 20 mM CaCl$_2$ solution. For this experiment, 10, 20, 50, 60, and 75 mg/mL solutions of Antibody M1 were prepared in 20 mM CaCl$_2$. A plot of OD400 nm versus Antibody M1 concentration is shown in FIG. 18. These data show that higher order structure increases with increasing Antibody M1 concentration.

Several observations can be made regarding all the data for Example 5. The opalescence effect is salt dependent in the following manner: NaCl>Na$_2$HPO$_4$>MgCl$_2$>CaCl$_2$. For a given protein concentration, opalescence will initially increase and then either plateau or drop as the salt concentration is increased. Opalescence increases with protein concentration. All the salts evaluated gelled Antibody M1 at 2-8° C. and the timing of gelation was salt dependent and appeared to be related to the level of opalescence.

The antibody used in the present invention is preferably Antibody M1 (also referred to herein as "Myo-029"), Antibody M2, and Antibody M3. Where the ionic strength of an antibody preparation (preferably containing Antibody M1, Antibody M2, or Antibody M3) is to be reduced or decreased in accordance with the present invention, the reduction or decrease in the ionic strength is normally carried out so that ratio of the ionic strength to the antibody concentration is reduced.

All publications, patent applications, patents, and other references mentioned herein are incorporated by reference herein in their entirety.

Other embodiments are within the scope of the following claims.

What is claimed is:

1. A method for decreasing the opalescence of an antibody preparation, the method comprising:
    (a) determining a second virial coefficient of an antibody in the antibody preparation; and
    (b) if the second virial coefficient of the antibody is negative, reducing the ionic strength of the antibody preparation such that the opalescence of the antibody preparation is reduced.

2. The method of claim 1, wherein the antibody comprises a human, humanized, chimeric, CDR-grafted, or an in vitro generated antibody, or an antigen-binding fragment thereof.

3. The method of claim 1, wherein the antibody comprises an antibody having IgG1 or an IgG4 heavy chain constant region.

4. The method of claim 1, wherein the second virial coefficient of the antibody is determined at a salt concentration ranging from about 50 to 200 mM.

5. The method of claim 4, wherein the second virial coefficient of the antibody is determined to be about $-1$ to $-10 \times 10^{-3}$, or about $-1$ to $-10 \times 10^{-4}$ mol-mg/g$^2$ at 100 mM sodium chloride.

6. The method of claim 1, wherein the antibody is present at a concentration of about 5 to 300 mg/ml.

7. The method of claim 1, wherein the ionic strength of the antibody preparation is reduced by decreasing the concentration of a salt present in the preparation.

8. The method of claim 7, wherein the salt present in the preparation is selected from the group consisting of sodium chloride, calcium chloride, magnesium chloride and sodium phosphate.

9. The method of claim 7, wherein the concentration of the salt is reduced to at least about two-, three-, five-, ten- or one hundred-fold lower than the initial concentration in the antibody preparation.

10. The method of claim 7, wherein the ionic strength of the antibody preparation is reduced by replacing a first salt with a second salt, wherein the first salt is NaCl, and the second salt is selected from the group consisting of Na$_2$HPO$_4$, MgCl$_2$, and CaCl$_2$.

11. The method of claim 7, wherein the ionic strength of the antibody preparation is reduced by replacing a first salt with a second salt, wherein the first salt is Na$_2$HPO$_4$, and the second salt is selected from the group consisting of MgCl$_2$ and CaCl$_2$.

12. The method of claim 1, wherein the ionic strength of the antibody preparation is reduced by ultra-filtration or dialysis.

13. The method of claim 1, wherein the ionic strength of the antibody preparation is reduced in a process of purifying the antibody, wherein the process of purifying the antibody comprises one or more of centrifugation, filtration, chromatography, lyophilization or reconstitution.

14. The method of claim 1, further comprising evaluating the opalescence of the antibody preparation.

15. The method of claim 14, wherein the opalescence of the antibody preparation is evaluated by determining the turbidity of the solution, a change in the second virial coefficient of the antibody, or a change in the formation of high molecular weight species.

16. The method of claim 15, wherein the opalescence is reduced to about 2 or 1 European Pharmacopoeia standard or less.

17. The method of claim 15, wherein the second virial coefficient changes from about $-1$ to $-10 \times 10^{-3}$ to about $-1$ to $-10 \times 10^{-4}$.

18. The method of claim 15, wherein the high molecular weight species is reduced by an amount of about two-, three-, four-, five-, six-, seven-, eight-, nine-, ten-, fifty- or one hundred-fold.

19. The method of claim 1, wherein the second virial coefficient of the antibody is determined by a static light scattering and Zimm analysis.

20. A method for reducing the formation of high molecular weight species in an antibody preparation, the method comprising:
    (a) providing an antibody preparation comprising an antibody determined to have a negative second virial coefficient;
    (b) reducing the ionic strength of the antibody preparation such that the high molecular weight species in the antibody preparation are reduced.

21. The method of claim 20, wherein the antibody comprises a human, humanized, chimeric, CDR-grafted, or an in vitro generated antibody, or an antigen-binding fragment thereof.

22. The method of claim 20, wherein the antibody comprises an IgG1 or an IgG4 heavy chain constant region.

23. The method of claim 20, wherein the antibody of the antibody preparation has a negative second virial coefficient in a salt concentration ranging from about 50 to 200 mM.

24. The method of claim 23, wherein the second virial coefficient is about $-1$ to $-10 \times 10^{-3}$, or about $-1$ to $-10 \times 10^{-4}$ mol-mg/g$^2$ in an antibody preparation containing 100 mM sodium chloride.

25. The method of claim 20, wherein the antibody is present at a concentration of about 5 to 300 mg/ml.

26. The method of claim 20, wherein the ionic strength of the antibody preparation is reduced by decreasing the concentration of a salt present in the preparation.

27. The method of claim 26, wherein the salt present in the preparation is selected from the group consisting of sodium chloride, calcium chloride, magnesium chloride and sodium phosphate.

28. The method of claim 26, wherein the concentration of the salt is reduced to at least about two-, three-, five-, ten- or one hundred-fold lower than the initial concentration in the antibody preparation.

29. The method of claim 26, wherein the ionic strength of the antibody preparation is reduced by replacing a first salt with a second salt, wherein the first salt is NaCl, and the second salt is selected from the group consisting of Na$_2$HPO$_4$, MgCl$_2$, and CaCl$_2$.

30. The method of claim 26, wherein the ionic strength of the antibody preparation is reduced by replacing a first salt with a second salt, wherein the first salt is Na$_2$HPO$_4$, and the second salt is selected from the group consisting of MgCl$_2$ and CaCl$_2$.

31. The method of claim 20, wherein the ionic strength of the antibody preparation is reduced by ultra-filtration or dialysis.

32. The method of claim 20, wherein the ionic strength of the antibody preparation is reduced in a process of purifying the antibody, wherein the process of purifying the antibody comprises one or more of centrifugation, filtration, chromatography, lyophilization or reconstitution.

33. The method of claim 20, further comprising evaluating the opalescence of the antibody preparation.

34. The method of claim 33, wherein the opalescence of the antibody preparation is evaluated by determining the turbidity of the solution, a change in the second virial coefficient of the antibody, or a change in the formation of high molecular weight species.

35. The method of claim 34, wherein the opalescence is reduced to about 2 or 1 European Pharmacopoeia standard or less.

36. The method of claim 34, wherein the second virial coefficient changes from about $-1$ to $-10 \times 10^{-3}$ to about $-1$ to $-10 \times 10^{-4}$.

37. The method of claim 20, wherein the high molecular weight species is reduced by an amount of about two-, three-, four-, five-, six-, seven-, eight-, nine-, ten-, fifty- or one hundred-fold.

38. A method of decreasing the formation of high molecular weight species in an antibody preparation, the method comprising:
(a) providing an antibody preparation comprising an antibody determined to have a negative second virial coefficient in 100 mM sodium chloride solution;
(b) reducing the ionic strength in the antibody preparation such that the formation of high molecular weight species in the antibody preparation is reduced.

39. A method of improving the efficiency of a purification process of an antibody in an antibody preparation, the method comprising:
evaluating whether the antibody in the antibody preparation has a negative second virial coefficient at one or more salt concentrations;
reducing the ionic strength in the antibody preparation, such that the high molecular weight species in the antibody preparation is reduced, thereby improving the efficiency of a purification process of an antibody preparation.

40. The method of claim 39, wherein the ionic strength of the antibody preparation is reduced by one or more steps selected from filtration, replacing a salt used in the antibody preparation with a lower opalescent inducer, or reducing the concentration of a salt present in the purification process.

* * * * *